(12) United States Patent
McMahon et al.

(10) Patent No.: US 11,724,051 B2
(45) Date of Patent: Aug. 15, 2023

(54) SYSTEMS AND METHODS FOR DETECTING AN INTENTIONAL LEAK CHARACTERISTIC CURVE FOR A RESPIRATORY THERAPY SYSTEM

(71) Applicant: ResMed Sensor Technologies Limited, Dublin (IE)

(72) Inventors: Stephen McMahon, Dublin (IE); Anna Rice, Dublin (IE); Graeme Alexander Lyon, Dublin (IE); Redmond Shouldice, Dublin (IE)

(73) Assignee: ResMed Sensor Technologies Limited, Dublin (IE)

( * ) Notice: Subject to any disclaimer, the term of this patent is extended or adjusted under 35 U.S.C. 154(b) by 0 days.

(21) Appl. No.: 17/801,096

(22) PCT Filed: Mar. 5, 2021

(86) PCT No.: PCT/IB2021/051884
§ 371 (c)(1),
(2) Date: Aug. 19, 2022

(87) PCT Pub. No.: WO2021/176426
PCT Pub. Date: Sep. 10, 2021

(65) Prior Publication Data
US 2023/0085305 A1     Mar. 16, 2023

Related U.S. Application Data

(60) Provisional application No. 63/108,837, filed on Nov. 2, 2020, provisional application No. 63/072,768, filed
(Continued)

(51) Int. Cl.
*A61M 16/00* (2006.01)

(52) U.S. Cl.
CPC ... *A61M 16/024* (2017.08); *A61M 2016/0027* (2013.01); *A61M 2016/0036* (2013.01); *A61M 2205/15* (2013.01); *A61M 2230/42* (2013.01)

(58) Field of Classification Search
CPC ....... A61B 5/083; A61B 5/087; A61B 5/4818; A61B 5/4836; A61B 5/7264;
(Continued)

(56) References Cited

U.S. PATENT DOCUMENTS

2007/0215146 A1* 9/2007 Douglas ................ A61M 16/06
128/200.24
2010/0186741 A1* 7/2010 Aylsworth ............ A61M 16/12
128/203.29
(Continued)

FOREIGN PATENT DOCUMENTS

JP     2004-506499 A     3/2004
JP     2009-506833 A     2/2009
(Continued)

OTHER PUBLICATIONS

International Search Report in International Patent Application No. PCT/IB2021/051884 dated May 31, 2021 (7 pp.).
(Continued)

*Primary Examiner* — Annette Dixon
(74) *Attorney, Agent, or Firm* — Nixon Peabody LLP

(57) ABSTRACT

A plurality of flow rate values associated with pressurized air directed to an airway of a user of a respiratory therapy system is received. A plurality of pressure values associated with the pressurized air directed to the airway of the user is received. A first time associated with a first breath of the user and a second time associated with a second breath of the user are identified. The plurality of flow rate values is filtered based at least in part on the identified first time and the identified second time. The filtering produces a subset of the
(Continued)

plurality of flow rate values. An intentional leak characteristic curve for the respiratory therapy system is determined using at least two of the subset of the plurality of flow rate values and the corresponding pressure values for the at least two of the subset of the plurality of flow rate values.

34 Claims, 17 Drawing Sheets

Related U.S. Application Data on Aug. 31, 2020, provisional application No. 62/986,431, filed on Mar. 6, 2020.

(58) Field of Classification Search
CPC .......... A61M 16/0051; A61M 16/0057; A61M 16/0066; A61M 16/0069; A61M 16/024; A61M 16/06; A61M 16/0677; A61M 16/0875; A61M 16/12; A61M 16/16; A61M 2016/0021; A61M 2016/0027; A61M 2016/0036; A61M 2016/0039; A61M 2016/0042; A61M 2202/0208; A61M 2205/15; A61M 2205/18; A61M 2205/3553; A61M 2205/50; A61M 2205/502; A61M 2210/0618; A61M 2210/0625; A61M 2230/435
See application file for complete search history.

(56) References Cited

U.S. PATENT DOCUMENTS

| | | | |
|---|---|---|---|
| 2014/0088373 | A1 | 3/2014 | Phillips et al. |
| 2017/0312463 | A1 | 11/2017 | Chang et al. |

FOREIGN PATENT DOCUMENTS

| | | | |
|---|---|---|---|
| JP | 2013-532565 | A | 8/2013 |
| JP | 2018-507748 | A | 3/2018 |
| WO | 9806449 | A1 | 2/1998 |
| WO | 2010085895 | A1 | 8/2010 |
| WO | 2012/012835 | A2 | 2/2012 |
| WO | 2014047310 | A1 | 3/2014 |
| WO | 2016/061629 | A1 | 4/2016 |
| WO | 2016145483 | A1 | 9/2016 |
| WO | 2017/132726 | A1 | 8/2017 |
| WO | 2018/050913 | A1 | 3/2018 |
| WO | 2019/122413 | A1 | 6/2019 |
| WO | 2019/122414 | A1 | 6/2019 |
| WO | 2020/104465 | A2 | 5/2020 |
| WO | 2021072486 | A1 | 4/2021 |

OTHER PUBLICATIONS

Written Opinion in International Patent Application No. PCT/IB2021/051884 dated May 3, 2021 (10 pp.).

JP Office Action for Application No. 2022-553698, dated Feb. 7, 2023 (English translation) 4 pp.

\* cited by examiner

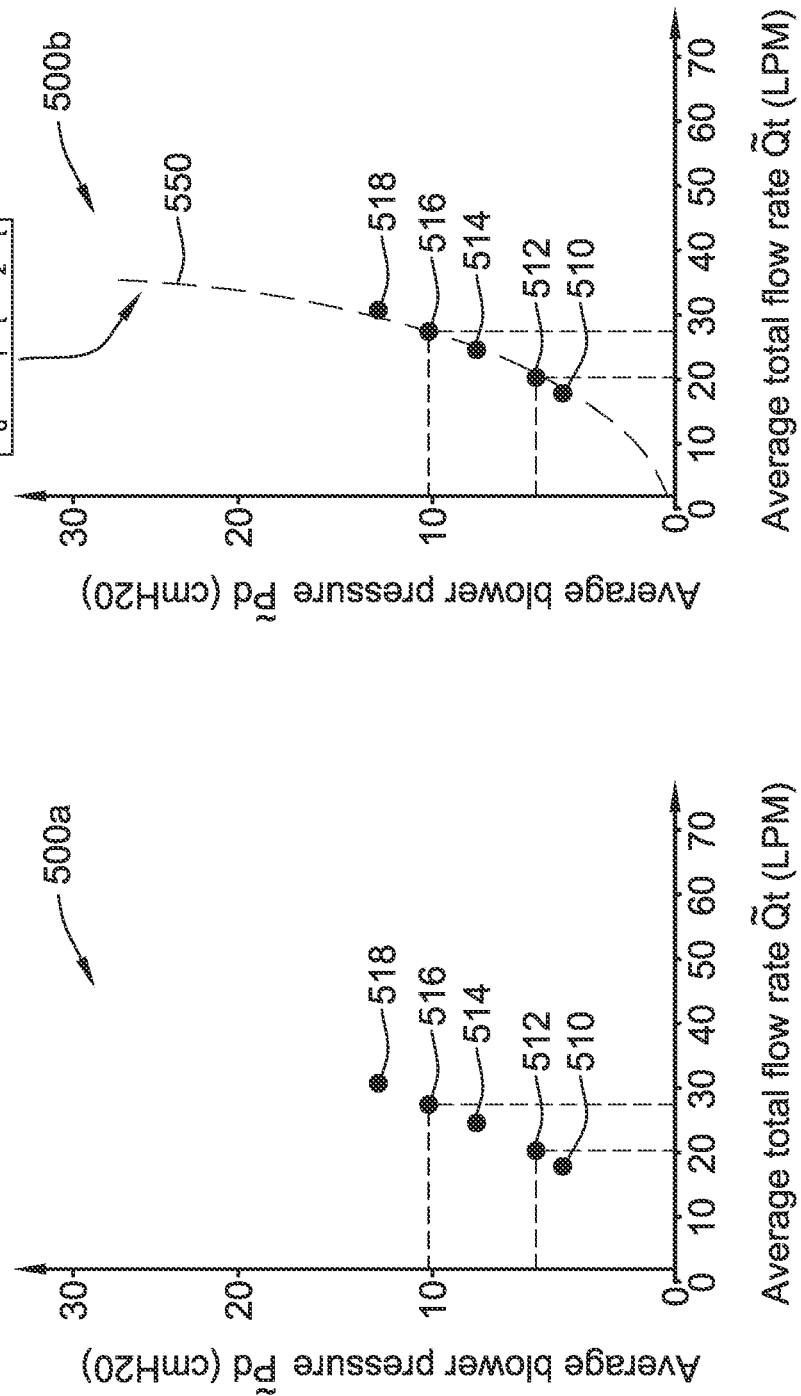

US 11,724,051 B2

SYSTEMS AND METHODS FOR DETECTING AN INTENTIONAL LEAK CHARACTERISTIC CURVE FOR A RESPIRATORY THERAPY SYSTEM

CROSS-REFERENCE TO RELATED APPLICATIONS

This application is a U.S. National Stage of International Application No. PCT/IB2021/051884, filed Mar. 5, 2021, which claims the benefit of, and priority to, U.S. Provisional Patent Application No. 62/986,431 filed on Mar. 6, 2020, U.S. Provisional Patent Application No. 63/072,768 filed on Aug. 31, 2020, and U.S. Provisional Patent Application No. 63/108,837 filed on Nov. 2, 2020, each which is hereby incorporated by reference herein in its entirety.

TECHNICAL FIELD

The present disclosure relates generally to respiratory therapy systems, and more particularly, to systems and methods for detecting an intentional characteristic curve for a respiratory therapy system.

BACKGROUND

Currently, the amount of leak in a mask is estimated based on a generic curve for each type of mask. The types of mask can be broken down into three general categories: full face, nasal, and pillows. Due to manufacturing tolerances in the masks, the generic curves are not always as accurate as desired. This may in turn lead to inaccurate estimation of the intentional leak. Thus, a more accurate curve that is customized for each mask for each user is desired. The present disclosure is directed to solving these and other problems.

SUMMARY

According to some implementations of the present disclosure, a method for determining an intentional leak characteristic curve for a respiratory therapy system is disclosed as follows. Flow rate data is received. The flow rate data is associated with a plurality of flow rate values of pressurized air directed to an airway of a user of the respiratory therapy system. Pressure data is received. The pressure data is associated with a plurality of pressure values of the pressurized air. A first Cartesian coordinate is generated. The first Cartesian coordinate has a first X value based at least on a first portion of the plurality of flow rate values and has a first Y value based at least on a first portion of the plurality of pressure values. A second Cartesian coordinate is generated. The second Cartesian coordinate has a second X value based at least on a second portion of the plurality of flow rate values and has a second Y value based at least on a second portion of the plurality of pressure values. Based at least in part on the generated first Cartesian coordinate and the generated second Cartesian coordinate, the intentional leak characteristic curve for the respiratory therapy system is determined.

According to some implementations of the present disclosure, a method is disclosed as follows. Using a pressure generator of a respiratory therapy system, a flow of pressurized air is supplied to an airway of a user for a first time period. The flow of pressurized air has a first nominal pressure value. Using a flow sensor positioned within the respiratory therapy system, a first plurality of flow rate values for the first time period is generated. Using a pressure sensor positioned within the respiratory therapy system, a first plurality of pressure values for the first time period is generated. A first Cartesian coordinate is determined. The first Cartesian coordinate has a first X value based on at least a first flow rate value of the first plurality of flow rate values. The first Cartesian coordinate has a first Y value based on at least a first pressure value of the first plurality of pressure values. The supplied flow of pressurized air is adjusted to a second nominal pressure value for a second time period. The second nominal pressure value is different from the first nominal pressure value. Using the flow sensor positioned within the respiratory therapy system, a second plurality of flow rate values for the second time period is generated. Using the pressure sensor positioned within the respiratory therapy system, a second plurality of pressure values for the second time period is generated. A second Cartesian coordinate is generated. The second Cartesian coordinate has a second X value based on at least a second flow rate value of the second plurality of flow rate values. The second Cartesian coordinate has a second Y value based on at least a second pressure value of the second plurality of pressure values. Based at least in part on the generated first Cartesian coordinate and the generated second Cartesian coordinate, an intentional leak characteristic curve associated with the respiratory therapy system is determined.

According to some implementations of the present disclosure, a method is disclosed as follows. Using a pressure generator of a respiratory therapy system, a flow of pressurized air is supplied to an airway of a user for a first time period. The flow of pressurized air has a first nominal pressure value. Using a flow sensor positioned within the respiratory therapy system, a first plurality of flow rate values for the first time period is generated. The first Cartesian coordinate has a first X value based on at least a first flow rate value of the first plurality of flow rate values. The first Cartesian coordinate has a first Y value based at least on the first nominal pressure value. The supplied flow of pressurized air is adjusted to a second nominal pressure value for a second time period. The second nominal pressure value is different from the first nominal pressure value. Using the flow sensor positioned within the respiratory therapy system, a second plurality of flow rate values for the second time period is generated. A second Cartesian coordinate is generated. The second Cartesian coordinate has a second X value based on at least a second flow rate value of the second plurality of flow rate values. The second Cartesian coordinate has a second Y value based at least on the second nominal pressure value. Based at least in part on the generated first Cartesian coordinate and the generated second Cartesian coordinate, an intentional leak characteristic curve associated with the respiratory therapy system is determined.

According to some implementations of the present disclosure, a method for determining an intentional leak characteristic curve for a respiratory therapy system is disclosed as follows. A plurality of flow rate values associated with pressurized air directed to an airway of a user of the respiratory therapy system is received. A plurality of pressure values associated with the pressurized air directed to the airway of the user is received. Each of the plurality of pressure values corresponds to a respective one of the plurality of flow rate values. A first time associated with a first breath of the user and a second time associated with a second breath of the user are identified. The plurality of flow rate values is filtered based at least in part on the identified first time and the identified second time. The filtering produces a subset of the plurality of flow rate values. The intentional leak characteristic curve for the respiratory therapy system is determined using at least two of the subset of the plurality of flow rate values and the corresponding pressure values for said at least two of the subset of the plurality of flow rate values.

According to some implementations of the present disclosure, a system includes a control system and a memory. The control system includes one or more processors. The memory has stored thereon machine readable instructions. The control system is coupled to the memory. Any one of the methods disclosed above is implemented when the machine executable instructions in the memory are executed by at least one of the one or more processors of the control system.

According to some implementations of the present disclosure, a system for determining an intentional leak characteristic curve for a respiratory therapy system is disclosed as follows. The system includes a control system configured to implement any one of the methods disclosed above.

According to some implementations of the present disclosure, a computer program product comprising instructions which, when executed by a computer, cause the computer to carry out any one of the methods disclosed above. In some implementations, the computer program product is a non-transitory computer readable medium.

The foregoing and additional aspects and implementations of the present disclosure will be apparent to those of ordinary skill in the art in view of the detailed description of various embodiments and/or implementations, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

FIG. 5A illustrates plotted Cartesian coordinates representing average device pressure and average total flow rate expressed as liters per minute, according to some implementations of the present disclosure.

FIG. 5B illustrates a fitted characteristic curve over the plotted Cartesian coordinates of FIG. 5A, according to some implementations of the present disclosure.

Figure 1:
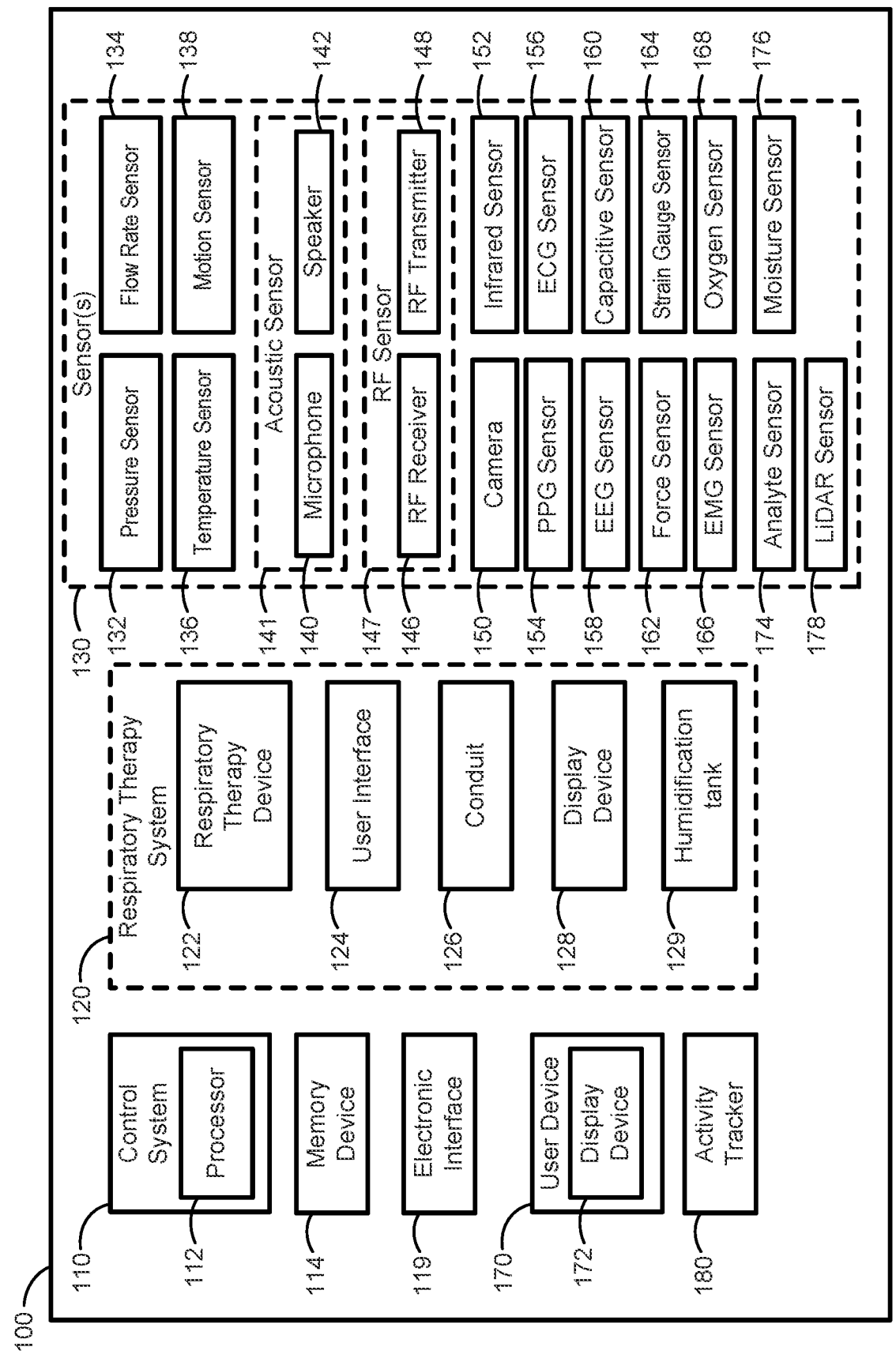
FIG. 1 is a functional block diagram of a system for determining one or more sleep-related parameters for a sleep session, according to some implementations of the present disclosure.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

The present disclosure is described with reference to the attached figures, where like reference numerals are used throughout the figures to designate similar or equivalent elements. The figures are not drawn to scale, and are provided merely to illustrate the instant disclosure. Several aspects of the disclosure are described below with reference to example applications for illustration.

A conventional method of intentional leak estimation in a respiratory therapy system is based on the characterization of the mask vent-flow with respect to mask pressure. Each mask type (full face, nasal, or pillows) is assigned a generalized vent-flow curve, such as the amount of flow through the mask vent for a given pressure. This is referred to as intentional leak or expected leak. For example, when the mask pressure is 30 cmH$_2$O, the full face mask vent flow is approximately 70 L/min; the nasal mask vent flow is approximately 60 L/min; and the pillows mask vent flow is approximately 56 L/min.

These generalized vent-flow curves are often pre-calculated and programmed into a look-up table, and selected by the system based on a user input for the mask type. Therefore, the correct mask setting needs to be selected, which may not always be the case. In addition, manufacturing tolerances can lead to inaccuracies in the leak estimate. Thus, a need exists to improve reporting of unintentional leak associated with the respiratory therapy system, with custom models of the mask vent-flow curves, which are computed based on measured mask pressure and measured flow rate.

Referring to FIG. 1, a system 100, according to some implementations of the present disclosure, is illustrated. The system 100 includes a control system 110, a memory device 114, an electronic interface 119, one or more sensors 130, and one or more user devices 170. In some implementations, the system 100 further optionally includes a respiratory therapy system 120, and an activity tracker 180.

The control system 110 includes one or more processors 112 (hereinafter, processor 112). The control system 110 is generally used to control (e.g., actuate) the various components of the system 100 and/or analyze data obtained and/or generated by the components of the system 100. The processor 112 can be a general or special purpose processor or microprocessor. While one processor 112 is illustrated in FIG. 1, the control system 110 (or any other control system) or a portion of the control system 110 such as the processor 112 (or any other processor(s) or portion(s) of any other control system), can be used to carry out one or more steps of any of the methods described and/or claimed herein. The control system 110 can include any suitable number of processors (e.g., one processor, two processors, five processors, ten processors, etc.) that can be in a single housing, or located remotely from each other. The control system 110 can be coupled to and/or positioned within, for example, a housing of the user device 170, a portion (e.g., a housing) of the respiratory therapy system 120, and/or within a housing of one or more of the sensors 130. The control system 110 can be centralized (within one such housing) or decentralized (within two or more of such housings, which are physically distinct). In such implementations including two or more housings containing the control system 110, such housings can be located proximately and/or remotely from each other.

The memory device 114 stores machine-readable instructions that are executable by the processor 112 of the control system 110. The memory device 114 can be any suitable computer readable storage device or media, such as, for example, a random or serial access memory device, a hard drive, a solid state drive, a flash memory device, etc. While one memory device 114 is shown in FIG. 1, the system 100 can include any suitable number of memory devices 114 (e.g., one memory device, two memory devices, five memory devices, ten memory devices, etc.). The memory device 114 can be coupled to and/or positioned within a housing of a respiratory therapy device 122 of the respiratory therapy system 120, within a housing of the user device 170, within a housing of one or more of the sensors 130, or any combination thereof. Like the control system 110, the memory device 114 can be centralized (within one such housing) or decentralized (within two or more of such housings, which are physically distinct).

In some implementations, the memory device 114 stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a geographic location of the user, a relationship status, a family history of insomnia or sleep apnea, an employment status of the user, an educational status of the user, a socioeconomic status of the user, or any combination thereof. The medical information can include, for example, information indicative of one or more medical conditions associated with the user, medication usage by the user, or both. The medical information data can further include a multiple sleep latency test (MSLT) result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

The electronic interface 119 is configured to receive data (e.g., physiological data and/or audio data) from the one or more sensors 130 such that the data can be stored in the memory device 114 and/or analyzed by the processor 112 of the control system 110. The electronic interface 119 can communicate with the one or more sensors 130 using a wired connection or a wireless connection (e.g., using an RF communication protocol, a Wi-Fi communication protocol, a Bluetooth communication protocol, over a cellular network, etc.). The electronic interface 119 can include an antenna, a receiver (e.g., an RF receiver), a transmitter (e.g., an RF transmitter), a transceiver, or any combination thereof. The electronic interface 119 can also include one or more processors and/or one more memory devices that are the same as, or similar to, the processor 112 and the memory device 114 described herein. In some implementations, the electronic interface 119 is coupled to or integrated in the user device 170. In other implementations, the electronic interface 119 is coupled to or integrated (e.g., in a housing) with the control system 110 and/or the memory device 114.

As noted above, in some implementations, the system 100 optionally includes a respiratory therapy system 120 (also referred to as a respiratory therapy system). The respiratory therapy system 120 can include a respiratory pressure therapy (RPT) device 122 (referred to herein as respiratory therapy device 122), a user interface 124, a conduit 126 (also referred to as a tube or an air circuit), a display device 128, a humidification tank 129 or any combination thereof. In some implementations, the control system 110, the memory device 114, the display device 128, one or more of the sensors 130, and the humidification tank 129 are part of the respiratory therapy device 122. Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory therapy system 120 is generally used to treat individuals suffering from one or more sleep-related respiratory disorders (e.g., obstructive sleep apnea, central sleep apnea, or mixed sleep apnea).

The respiratory therapy device 122 is generally used to generate pressurized air that is delivered to a user (e.g., using one or more motors that drive one or more compressors). In some implementations, the respiratory therapy device 122 generates continuous constant air pressure that is delivered to the user. In other implementations, the respiratory therapy device 122 generates two or more predetermined pressures (e.g., a first predetermined air pressure and a second predetermined air pressure). In still other implementations, the respiratory therapy device 122 is configured to generate a variety of different air pressures within a predetermined range. For example, the respiratory therapy device 122 can deliver at least about 6 cmH$_2$O, at least about 10 cmH$_2$O, at least about 20 cmH$_2$O, between about 6 cmH$_2$O and about 10 cmH$_2$O, between about 7 cmH$_2$O and about 12 cmH$_2$O, etc. The respiratory therapy device 122 can also deliver pressurized air at a predetermined flow rate between, for example, about −20 L/min and about 150 L/min, while maintaining a positive pressure (relative to the ambient pressure).

The user interface 124 engages a portion of the user's face and delivers pressurized air from the respiratory therapy device 122 to the user's airway to aid in preventing the airway from narrowing and/or collapsing during sleep. This may also increase the user's oxygen intake during sleep. Generally, the user interface 124 engages the user's face such that the pressurized air is delivered to the user's airway via the user's mouth, the user's nose, or both the user's mouth and nose. Together, the respiratory therapy device 122, the user interface 124, and the conduit 126 form an air pathway fluidly coupled with an airway of the user. The pressurized air also increases the user's oxygen intake during sleep.

Depending upon the therapy to be applied, the user interface 124 may form a seal, for example, with a region or portion of the user's face, to facilitate the delivery of gas at a pressure at sufficient variance with ambient pressure to effect therapy, for example, at a positive pressure of about 10 cmH$_2$O relative to ambient pressure. For other forms of therapy, such as the delivery of oxygen, the user interface may not include a seal sufficient to facilitate delivery to the airways of a supply of gas at a positive pressure of about 10 cmH$_2$O.

Figure 2:
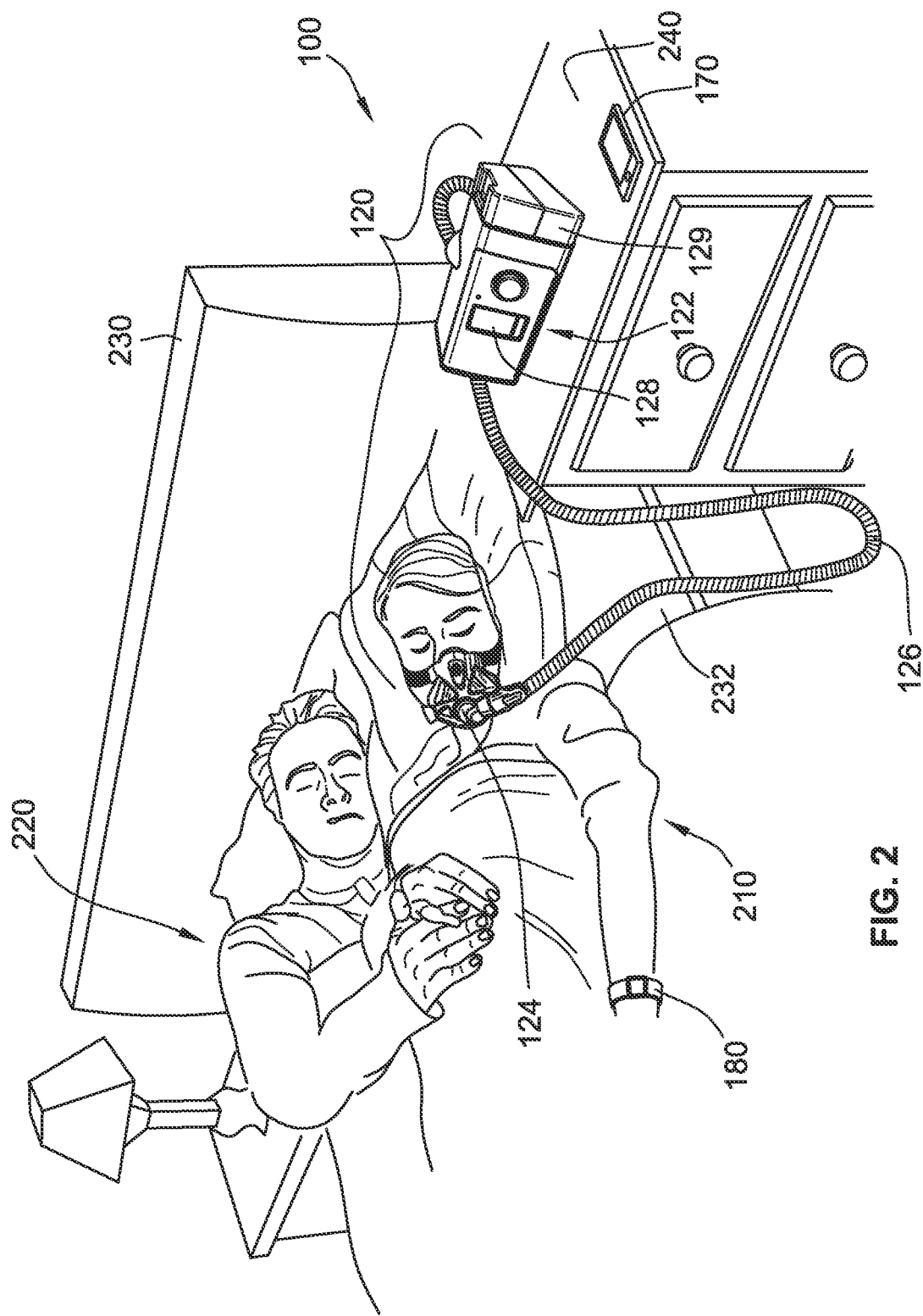
FIG. 2 is a perspective view of at least a portion of the system of FIG. 1, a user, and a bed partner, according to some implementations of the present disclosure.

As shown in FIG. 2, in some implementations, the user interface 124 is a facial mask (e.g., a full face mask) that covers the nose and mouth of the user. Alternatively, the user interface 124 is a nasal mask that provides air to the nose of the user or a nasal pillow mask that delivers air directly to the nostrils of the user. The user interface 124 can include a plurality of straps (e.g., including hook and loop fasteners) forming, for example, a headgear for aiding in positioning and/or stabilizing the interface on a portion of the user (e.g., the face) and a conformal cushion (e.g., silicone, plastic, foam, etc.) that aids in providing an air-tight seal between the user interface 124 and the user. The user interface 124 can also include one or more vents for permitting the escape of carbon dioxide and other gases exhaled by the user 210. In other implementations, the user interface 124 includes a mouthpiece (e.g., a night guard mouthpiece molded to conform to the teeth of the user, a mandibular repositioning device, etc.).

The conduit 126 (also referred to as an air circuit or tube) allows the flow of air between two components of a respiratory therapy system 120, such as the respiratory therapy device 122 and the user interface 124. In some implementations, there can be separate limbs of the conduit for inhalation and exhalation. In other implementations, a single limb conduit is used for both inhalation and exhalation.

One or more of the respiratory therapy device 122, the user interface 124, the conduit 126, the display device 128, and the humidification tank 129 can contain one or more sensors (e.g., a pressure sensor, a flow rate sensor, or more generally any of the other sensors 130 described herein). These one or more sensors can be used, for example, to measure the air pressure and/or flow rate of pressurized air supplied by the respiratory therapy device 122.

The display device 128 is generally used to display image(s) including still images, video images, or both and/or information regarding the respiratory therapy device 122. For example, the display device 128 can provide information regarding the status of the respiratory therapy device 122 (e.g., whether the respiratory therapy device 122 is on/off, the pressure of the air being delivered by the respiratory therapy device 122, the temperature of the air being delivered by the respiratory therapy device 122, etc.) and/or other information (e.g., a sleep score and/or a therapy score, also referred to as a myAir™ score, such as described in WO 2016/061629, which is hereby incorporated by reference herein in its entirety; the current date/time; personal information for the user 210; etc.). In some implementations, display device 128 acts as a human-machine interface (HMI) that includes a graphic user interface (GUI) configured to display the image(s) as an input interface. The display device 128 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory therapy device 122.

The humidification tank 129 is coupled to or integrated in the respiratory therapy device 122, and includes a reservoir of water that can be used to humidify the pressurized air delivered from the respiratory therapy device 122. The respiratory therapy device 122 can include a heater to heat the water in the humidification tank 129 in order to humidify the pressurized air provided to the user. Additionally, in some implementations, the conduit 126 can also include a heating element (e.g., coupled to and/or imbedded in the conduit 126) that heats the pressurized air delivered to the user. The humidification tank 129 can be fluidly coupled to a water vapor inlet of the air pathway and deliver water vapor into the air pathway via the water vapor inlet, or can be formed in-line with the air pathway as part of the air pathway itself.

In some implementations, the system 100 can be used to deliver at least a portion of a substance from the receptacle to the air pathway the user based at least in part on the physiological data, the sleep-related parameters, other data or information, or any combination thereof. Generally, modifying the delivery of the portion of the substance into the air pathway can include (i) initiating the delivery of the substance into the air pathway, (ii) ending the delivery of the portion of the substance into the air pathway, (iii) modifying an amount of the substance delivered into the air pathway, (iv) modifying a temporal characteristic of the delivery of the portion of the substance into the air pathway, (v) modifying a quantitative characteristic of the delivery of the portion of the substance into the air pathway, (vi) modifying any parameter associated with the delivery of the substance into the air pathway, or (vii) a combination of (i)-(vi).

Modifying the temporal characteristic of the delivery of the portion of the substance into the air pathway can include changing the rate at which the substance is delivered, starting and/or finishing at different times, continuing for different time periods, changing the time distribution or characteristics of the delivery, changing the amount distribution independently of the time distribution, etc. The independent time and amount variation ensures that, apart from varying the frequency of the release of the substance, one can vary the amount of substance released each time. In this manner, a number of different combination of release frequencies and release amounts (e.g., higher frequency but lower release amount, higher frequency and higher amount, lower frequency and higher amount, lower frequency and lower amount, etc.) can be achieved. Other modifications to the delivery of the portion of the substance into the air pathway can also be utilized.

The respiratory therapy system 120 can be used, for example, as a ventilator or as a positive airway pressure (PAP) system such as a continuous positive airway pressure (CPAP) system, an automatic positive airway pressure system (APAP), a bi-level or variable positive airway pressure system (BPAP or VPAP), or any combination thereof. The CPAP system delivers a predetermined air pressure (e.g., determined by a sleep physician) to the user. The APAP system automatically varies the air pressure delivered to the user based on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

Referring to FIG. 2, a portion of the system 100 (FIG. 1), according to some implementations, is illustrated. A user 210 of the respiratory therapy system 120 and a bed partner 220 are located in a bed 230 and are laying on a mattress 232. The user interface 124 (also referred to herein as a mask, e.g., a full face mask, a nasal mask, a nasal pillows mask, etc.) can be worn by the user 210 during a sleep session. The user interface 124 is fluidly coupled and/or connected to the respiratory therapy device 122 via the conduit 126. In turn, the respiratory therapy device 122 delivers pressurized air to the user 210 via the conduit 126 and the user interface 124 to increase the air pressure in the throat of the user 210 to aid in preventing the airway from closing and/or narrowing during sleep. The respiratory therapy device 122 can be positioned on a nightstand 240 that is directly adjacent to the bed 230 as shown in FIG. 2, or more generally, on any surface or structure that is generally adjacent to the bed 230 and/or the user 210.

Referring to back to FIG. 1, the one or more sensors 130 of the system 100 include a pressure sensor 132, a flow rate sensor 134, temperature sensor 136, a motion sensor 138, a microphone 140, a speaker 142, a radio-frequency (RF) receiver 146, a RF transmitter 148, a camera 150, an infrared sensor 152, a photoplethysmogram (PPG) sensor 154, an electrocardiogram (ECG) sensor 156, an electroencephalography (EEG) sensor 158, a capacitive sensor 160, a force sensor 162, a strain gauge sensor 164, an electromyography (EMG) sensor 166, an oxygen sensor 168, an analyte sensor 174, a moisture sensor 176, a LiDAR sensor 178, or any combination thereof. Generally, each of the one or more sensors 130 are configured to output sensor data that is received and stored in the memory device 114 or one or more other memory devices.

While the one or more sensors 130 are shown and described as including each of the pressure sensor 132, the flow rate sensor 134, the temperature sensor 136, the motion sensor 138, the microphone 140, the speaker 142, the RF receiver 146, the RF transmitter 148, the camera 150, the infrared sensor 152, the photoplethysmogram (PPG) sensor 154, the electrocardiogram (ECG) sensor 156, the electroencephalography (EEG) sensor 158, the capacitive sensor 160, the force sensor 162, the strain gauge sensor 164, the electromyography (EMG) sensor 166, the oxygen sensor 168, the analyte sensor 174, the moisture sensor 176, and the LiDAR sensor 178 more generally, the one or more sensors 130 can include any combination and any number of each of the sensors described and/or shown herein.

As described herein, the system 100 generally can be used to generate physiological data associated with a user (e.g., a user of the respiratory therapy system 120 shown in FIG. 2) during a sleep session. The physiological data can be analyzed to generate one or more sleep-related parameters, which can include any parameter, measurement, etc. related to the user during the sleep session. The one or more sleep-related parameters that can be determined for the user 210 during the sleep session include, for example, an Apnea-Hypopnea Index (AHI) score, a sleep score, a flow signal, a respiration signal, a respiration rate, an inspiration amplitude, an expiration amplitude, an inspiration-expiration ratio, a number of events per hour, a pattern of events, a stage, pressure settings of the respiratory therapy device 122, a heart rate, a heart rate variability, movement of the user 210, temperature, EEG activity, EMG activity, arousal, snoring, choking, coughing, whistling, wheezing, or any combination thereof.

The one or more sensors 130 can be used to generate, for example, physiological data, audio data, or both. Physiological data generated by one or more of the sensors 130 can be used by the control system 110 to determine a sleep-wake signal associated with the user 210 (FIG. 2) during the sleep session and one or more sleep-related parameters. The sleep-wake signal can be indicative of one or more sleep states, including wakefulness, relaxed wakefulness, microawakenings, or distinct sleep stages such as, for example, a rapid eye movement (REM) stage, a first non-REM stage (often referred to as "N1"), a second non-REM stage (often referred to as "N2"), a third non-REM stage (often referred to as "N3"), or any combination thereof. Methods for determining sleep states and/or sleep stages from physiological data generated by one or more sensors, such as the one or more sensors 130, are described in, for example, WO 2014/047310, US 2014/0088373, WO 2017/132726, WO 2019/122413, and WO 2019/122414, each of which is hereby incorporated by reference herein in its entirety.

In some implementations, the sleep-wake signal described herein can be timestamped to indicate a time that the user enters the bed, a time that the user exits the bed, a time that the user attempts to fall asleep, etc. The sleep-wake signal can be measured by the one or more sensors 130 during the sleep session at a predetermined sampling rate, such as, for example, one sample per second, one sample per 30 seconds, one sample per minute, etc. In some implementations, the sleep-wake signal can also be indicative of a respiration signal, a respiration rate, an inspiration amplitude, an expiration amplitude, an inspiration-expiration ratio, a number of events per hour, a pattern of events, pressure settings of the respiratory therapy device 122, or any combination thereof during the sleep session. The event(s) can include snoring, apneas, central apneas, obstructive apneas, mixed apneas, hypopneas, a mask leak (e.g., from the user interface 124), a restless leg, a sleeping disorder, choking, an increased heart rate, labored breathing, an asthma attack, an epileptic episode, a seizure, or any combination thereof. The one or more sleep-related parameters that can be determined for the user during the sleep session based on the sleep-wake signal include, for example, a total time in bed, a total sleep time, a sleep onset latency, a wake-after-sleep-onset parameter, a sleep efficiency, a fragmentation index, or any combination thereof. As described in further detail herein, the physiological data and/or the sleep-related parameters can be analyzed to determine one or more sleep-related scores.

Physiological data and/or audio data generated by the one or more sensors 130 can also be used to determine a respiration signal associated with a user during a sleep session. The respiration signal is generally indicative of respiration or breathing of the user during the sleep session. The respiration signal can be indicative of and/or analyzed to determine (e.g., using the control system 110) one or more sleep-related parameters, such as, for example, a respiration rate, a respiration rate variability, an inspiration amplitude, an expiration amplitude, an inspiration-expiration ratio, an occurrence of one or more events, a number of events per hour, a pattern of events, a sleep state, a sleet stage, an apnea-hypopnea index (AHI), pressure settings of the respiratory therapy device 122, or any combination thereof. The one or more events can include snoring, apneas, central apneas, obstructive apneas, mixed apneas, hypopneas, a mask leak (e.g., from the user interface 124), a cough, a restless leg, a sleeping disorder, choking, an increased heart rate, labored breathing, an asthma attack, an epileptic episode, a seizure, increased blood pressure, or any combination thereof. Many of the described sleep-related parameters are physiological parameters, although some of the sleep-related parameters can be considered to be non-physiological parameters. Other types of physiological and/or non-physiological parameters can also be determined, either from the data from the one or more sensors 130, or from other types of data As used herein, a sleep session can be defined in multiple ways. For example, a sleep session can be defined by an initial start time and an end time. In some implementations, a sleep session is a duration where the user is asleep, that is, the sleep session has a start time and an end time, and during the sleep session, the user does not wake until the end time. That is, any period of the user being awake is not included in a sleep session. From this first definition of sleep session, if the user wakes ups and falls asleep multiple times in the same night, each of the sleep intervals separated by an awake interval is a sleep session.

Alternatively, in some implementations, a sleep session has a start time and an end time, and during the sleep session, the user can wake up, without the sleep session ending, so long as a continuous duration that the user is awake is below an awake duration threshold. The awake duration threshold can be defined as a percentage of a sleep session. The awake duration threshold can be, for example, about twenty percent of the sleep session, about fifteen percent of the sleep session duration, about ten percent of the sleep session duration, about five percent of the sleep session duration, about two percent of the sleep session duration, etc., or any other threshold percentage. In some implementations, the awake duration threshold is defined as a fixed amount of time, such as, for example, about one hour, about thirty minutes, about fifteen minutes, about ten minutes, about five minutes, about two minutes, etc., or any other amount of time.

In some implementations, a sleep session is defined as the entire time between the time in the evening at which the user first entered the bed, and the time the next morning when user last left the bed. Put another way, a sleep session can be defined as a period of time that begins on a first date (e.g., Monday, Jan. 6, 2020) at a first time (e.g., 10:00 PM), that can be referred to as the current evening, when the user first enters a bed with the intention of going to sleep (e.g., not if the user intends to first watch television or play with a smart phone before going to sleep, etc.), and ends on a second date (e.g., Tuesday, Jan. 7, 2020) at a second time (e.g., 7:00 AM), that can be referred to as the next morning, when the user first exits the bed with the intention of not going back to sleep that next morning.

In some implementations, the user can manually define the beginning of a sleep session and/or manually terminate a sleep session. For example, the user can select (e.g., by clicking or tapping) one or more user-selectable element that is displayed on the display device 172 of the user device 170 (FIG. 1) to manually initiate or terminate the sleep session.

Generally, the sleep session includes any point in time after the user 210 has laid or sat down in the bed 230 (or another area or object on which they intend to sleep), and has turned on the respiratory therapy device 122 and donned the user interface 124. The sleep session can thus include time periods (i) when the user 210 is using the CPAP system but before the user 210 attempts to fall asleep (for example when the user 210 lays in the bed 230 reading a book); (ii) when the user 210 begins trying to fall asleep but is still awake; (iii) when the user 210 is in a light sleep (also referred to as stage 1 and stage 2 of non-rapid eye movement (NREM) sleep); (iv) when the user 210 is in a deep sleep (also referred to as slow-wave sleep, SWS, or stage 3 of NREM sleep); (v) when the user 210 is in rapid eye movement (REM) sleep; (vi) when the user 210 is periodically awake between light sleep, deep sleep, or REM sleep; or (vii) when the user 210 wakes up and does not fall back asleep.

The sleep session is generally defined as ending once the user 210 removes the user interface 124, turns off the respiratory therapy device 122, and gets out of bed 230. In some implementations, the sleep session can include additional periods of time, or can be limited to only some of the above-disclosed time periods. For example, the sleep session can be defined to encompass a period of time beginning when the respiratory therapy device 122 begins supplying the pressurized air to the airway or the user 210, ending when the respiratory therapy device 122 stops supplying the pressurized air to the airway of the user 210, and including some or all of the time points in between, when the user 210 is asleep or awake.

The pressure sensor 132 outputs pressure data that can be stored in the memory device 114 and/or analyzed by the processor 112 of the control system 110. In some implementations, the pressure sensor 132 is an air pressure sensor (e.g., barometric pressure sensor) that generates sensor data indicative of the respiration (e.g., inhaling and/or exhaling) of the user of the respiratory therapy system 120 and/or ambient pressure. In such implementations, the pressure sensor 132 can be coupled to or integrated in the respiratory therapy device 122. The pressure sensor 132 can be, for example, a capacitive sensor, an electromagnetic sensor, a piezoelectric sensor, a strain-gauge sensor, an optical sensor, a potentiometric sensor, or any combination thereof.

The flow rate sensor 134 outputs flow rate data that can be stored in the memory device 114 and/or analyzed by the processor 112 of the control system 110. Examples of flow rate sensors (such as, for example, the flow rate sensor 134) are described in International Publication No. WO 2012/012835, which is hereby incorporated by reference herein in its entirety. In some implementations, the flow rate sensor 134 is used to determine an air flow rate from the respiratory therapy device 122, an air flow rate through the conduit 126, an air flow rate through the user interface 124, or any combination thereof. In such implementations, the flow rate sensor 134 can be coupled to or integrated in the respiratory therapy device 122, the user interface 124, or the conduit 126. The flow rate sensor 134 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof. In some implementations, the flow rate sensor 134 is configured to measure a vent flow (e.g., intentional "leak"), an unintentional leak (e.g., mouth leak and/or mask leak), a patient flow (e.g., air into and/or out of lungs), or any combination thereof. In some implementations, the flow rate data can be analyzed to determine cardiogenic oscillations of the user. In one example, the pressure sensor 132 can be used to determine a blood pressure of a user.

The temperature sensor 136 outputs temperature data that can be stored in the memory device 114 and/or analyzed by the processor 112 of the control system 110. In some implementations, the temperature sensor 136 generates temperatures data indicative of a core body temperature of the user 210 (FIG. 2), a skin temperature of the user 210, a temperature of the air flowing from the respiratory therapy device 122 and/or through the conduit 126, a temperature in the user interface 124, an ambient temperature, or any combination thereof. The temperature sensor 136 can be, for example, a thermocouple sensor, a thermistor sensor, a silicon band gap temperature sensor or semiconductor-based sensor, a resistance temperature detector, or any combination thereof.

The motion sensor 138 outputs motion data that can be stored in the memory device 114 and/or analyzed by the processor 112 of the control system 110. The motion sensor 138 can be used to detect movement of the user 210 during the sleep session, and/or detect movement of any of the components of the respiratory therapy system 120, such as the respiratory therapy device 122, the user interface 124, or the conduit 126. The motion sensor 138 can include one or more inertial sensors, such as accelerometers, gyroscopes, and magnetometers. In some implementations, the motion sensor 138 alternatively or additionally generates one or more signals representing bodily movement of the user, from which may be obtained a signal representing a sleep state of the user; for example, via a respiratory movement of the user. In some implementations, the motion data from the motion sensor 138 can be used in conjunction with additional data from another sensor 130 to determine the sleep state of the user.

The microphone 140 outputs sound data that can be stored in the memory device 114 and/or analyzed by the processor 112 of the control system 110. The audio data generated by the microphone 140 is reproducible as one or more sound(s) during a sleep session (e.g., sounds from the user 210). The audio data form the microphone 140 can also be used to identify (e.g., using the control system 110) an event experienced by the user during the sleep session, as described in further detail herein. The microphone 140 can be coupled to or integrated in the respiratory therapy device 122, the user interface 124, the conduit 126, or the user device 170. In some implementations, the system 100 includes a plurality of microphones (e.g., two or more microphones and/or an array of microphones with beamforming) such that sound data generated by each of the plurality of microphones can be used to discriminate the sound data generated by another of the plurality of microphones.

The speaker 142 outputs sound waves that are audible to a user of the system 100 (e.g., the user 210 of FIG. 2). The speaker 142 can be used, for example, as an alarm clock or to play an alert or message to the user 210 (e.g., in response to an event). In some implementations, the speaker 142 can be used to communicate the audio data generated by the microphone 140 to the user. The speaker 142 can be coupled to or integrated in the respiratory therapy device 122, the user interface 124, the conduit 126, or the user device 170.

The microphone 140 and the speaker 142 can be used as separate devices. In some implementations, the microphone 140 and the speaker 142 can be combined into an acoustic sensor 141 (e.g., a SONAR sensor), as described in, for example, WO 2018/050913 and WO 2020/104465, each of which is hereby incorporated by reference herein in its entirety. In such implementations, the speaker 142 generates or emits sound waves at a predetermined interval and the microphone 140 detects the reflections of the emitted sound waves from the speaker 142. The sound waves generated or emitted by the speaker 142 have a frequency that is not audible to the human ear (e.g., below 20 Hz or above around 18 kHz) so as not to disturb the sleep of the user 210 or the bed partner 220 (FIG. 2). Based at least in part on the data from the microphone 140 and/or the speaker 142, the control system 110 can determine a location of the user 210 (FIG. 2) and/or one or more of the sleep-related parameters described in herein, such as, for example, a respiration signal, a respiration rate, an inspiration amplitude, an expiration amplitude, an inspiration-expiration ratio, a number of events per hour, a pattern of events, a sleep state, a sleep stage, pressure settings of the respiratory therapy device 122, or any combination thereof. In such a context, a sonar sensor may be understood to concern an active acoustic sensing, such as by generating and/or transmitting ultrasound and/or low frequency ultrasound sensing signals (e.g., in a frequency range of about 17-23 kHz, 18-22 kHz, or 17-18 kHz, for example), through the air. Such a system may be considered in relation to WO 2018/050913 and WO 2020/104465 mentioned above, each of which is hereby incorporated by reference herein in its entirety.

In some implementations, the sensors 130 include (i) a first microphone that is the same as, or similar to, the microphone 140, and is integrated in the acoustic sensor 141 and (ii) a second microphone that is the same as, or similar to, the microphone 140, but is separate and distinct from the first microphone that is integrated in the acoustic sensor 141.

The RF transmitter 148 generates and/or emits radio waves having a predetermined frequency and/or a predetermined amplitude (e.g., within a high frequency band, within a low frequency band, long wave signals, short wave signals, etc.). The RF receiver 146 detects the reflections of the radio waves emitted from the RF transmitter 148, and this data can be analyzed by the control system 110 to determine a location of the user 210 (FIG. 2) and/or one or more of the sleep-related parameters described herein. An RF receiver (either the RF receiver 146 and the RF transmitter 148 or another RF pair) can also be used for wireless communication between the control system 110, the respiratory therapy device 122, the one or more sensors 130, the user device 170, or any combination thereof. While the RF receiver 146 and RF transmitter 148 are shown as being separate and distinct elements in FIG. 1, in some implementations, the RF receiver 146 and RF transmitter 148 are combined as a part of an RF sensor 147 (e.g., a RADAR sensor). In some such implementations, the RF sensor 147 includes a control circuit. The specific format of the RF communication can be Wi-Fi, Bluetooth, or the like.

In some implementations, the RF sensor 147 is a part of a mesh system. One example of a mesh system is a Wi-Fi mesh system, which can include mesh nodes, mesh router(s), and mesh gateway(s), each of which can be mobile/movable or fixed. In such implementations, the Wi-Fi mesh system includes a Wi-Fi router and/or a Wi-Fi controller and one or more satellites (e.g., access points), each of which include an RF sensor that the is the same as, or similar to, the RF sensor 147. The Wi-Fi router and satellites continuously communicate with one another using Wi-Fi signals. The Wi-Fi mesh system can be used to generate motion data based on changes in the Wi-Fi signals (e.g., differences in received signal strength) between the router and the satellite(s) due to an object or person moving partially obstructing the signals. The motion data can be indicative of motion, breathing, heart rate, gait, falls, behavior, etc., or any combination thereof.

The camera 150 outputs image data reproducible as one or more images (e.g., still images, video images, thermal images, or any combination thereof) that can be stored in the memory device 114. The image data from the camera 150 can be used by the control system 110 to determine one or more of the sleep-related parameters described herein, such as, for example, one or more events (e.g., periodic limb movement or restless leg syndrome), a respiration signal, a respiration rate, an inspiration amplitude, an expiration amplitude, an inspiration-expiration ratio, a number of events per hour, a pattern of events, a sleep state, a sleep stage, or any combination thereof. Further, the image data from the camera 150 can be used to, for example, identify a location of the user, to determine chest movement of the user 210 (FIG. 2), to determine air flow of the mouth and/or nose of the user 210, to determine a time when the user 210 enters the bed 230 (FIG. 2), and to determine a time when the user 210 exits the bed 230. In some implementations, the camera 150 includes a wide angle lens or a fish eye lens.

The infrared (IR) sensor 152 outputs infrared image data reproducible as one or more infrared images (e.g., still images, video images, or both) that can be stored in the memory device 114. The infrared data from the IR sensor 152 can be used to determine one or more sleep-related parameters during a sleep session, including a temperature of the user 210 and/or movement of the user 210. The IR sensor 152 can also be used in conjunction with the camera 150 when measuring the presence, location, and/or movement of the user 210. The IR sensor 152 can detect infrared light having a wavelength between about 700 nm and about 1 mm, for example, while the camera 150 can detect visible light having a wavelength between about 380 nm and about 740 nm.

The PPG sensor 154 outputs physiological data associated with the user 210 (FIG. 2) that can be used to determine one or more sleep-related parameters, such as, for example, a heart rate, a heart rate variability, a cardiac cycle, respiration rate, an inspiration amplitude, an expiration amplitude, an inspiration-expiration ratio, estimated blood pressure parameter(s), or any combination thereof. The PPG sensor 154 can be worn by the user 210, embedded in clothing and/or fabric that is worn by the user 210, embedded in and/or coupled to the user interface 124 and/or its associated headgear (e.g., straps, etc.), etc.

The ECG sensor 156 outputs physiological data associated with electrical activity of the heart of the user 210. In some implementations, the ECG sensor 156 includes one or more electrodes that are positioned on or around a portion of the user 210 during the sleep session. The physiological data from the ECG sensor 156 can be used, for example, to determine one or more of the sleep-related parameters described herein.

The EEG sensor 158 outputs physiological data associated with electrical activity of the brain of the user 210. In some implementations, the EEG sensor 158 includes one or more electrodes that are positioned on or around the scalp of the user 210 during the sleep session. The physiological data from the EEG sensor 158 can be used, for example, to determine a sleep state and/or a sleep stage of the user 210 at any given time during the sleep session. In some implementations, the EEG sensor 158 can be integrated in the user interface 124 and/or the associated headgear (e.g., straps, etc.).

The capacitive sensor 160, the force sensor 162, and the strain gauge sensor 164 output data that can be stored in the memory device 114 and used by the control system 110 to determine one or more of the sleep-related parameters described herein. The EMG sensor 166 outputs physiological data associated with electrical activity produced by one or more muscles. The oxygen sensor 168 outputs oxygen data indicative of an oxygen concentration of gas (e.g., in the conduit 126 or at the user interface 124). The oxygen sensor 168 can be, for example, an ultrasonic oxygen sensor, an electrical oxygen sensor, a chemical oxygen sensor, an optical oxygen sensor, a pulse oximeter (e.g., $SpO_2$ sensor), or any combination thereof. In some implementations, the one or more sensors 130 also include a galvanic skin response (GSR) sensor, a blood flow sensor, a respiration sensor, a pulse sensor, a sphygmomanometer sensor, an oximetry sensor, or any combination thereof.

The analyte sensor 174 can be used to detect the presence of an analyte in the exhaled breath of the user 210. The data output by the analyte sensor 174 can be stored in the memory device 114 and used by the control system 110 to determine the identity and concentration of any analytes in the breath of the user 210. In some implementations, the analyte sensor 174 is positioned near a mouth of the user 210 to detect analytes in breath exhaled from the user 210's mouth. For example, when the user interface 124 is a facial mask that covers the nose and mouth of the user 210, the analyte sensor 174 can be positioned within the facial mask to monitor the user 210's mouth breathing. In other implementations, such as when the user interface 124 is a nasal mask or a nasal pillow mask, the analyte sensor 174 can be positioned near the nose of the user 210 to detect analytes in breath exhaled through the user's nose. In still other implementations, the analyte sensor 174 can be positioned near the user 210's mouth when the user interface 124 is a nasal mask or a nasal pillow mask. In this implementation, the analyte sensor 174 can be used to detect whether any air is inadvertently leaking from the user 210's mouth. In some implementations, the analyte sensor 174 is a volatile organic compound (VOC) sensor that can be used to detect carbon-based chemicals or compounds. In some implementations, the analyte sensor 174 can also be used to detect whether the user 210 is breathing through their nose or mouth. For example, if the data output by an analyte sensor 174 positioned near the mouth of the user 210 or within the facial mask (in implementations where the user interface 124 is a facial mask) detects the presence of an analyte, the control system 110 can use this data as an indication that the user 210 is breathing through their mouth.

The moisture sensor 176 outputs data that can be stored in the memory device 114 and used by the control system 110. The moisture sensor 176 can be used to detect moisture in various areas surrounding the user (e.g., inside the conduit 126 or the user interface 124, near the user 210's face, near the connection between the conduit 126 and the user interface 124, near the connection between the conduit 126 and the respiratory therapy device 122, etc.). Thus, in some implementations, the moisture sensor 176 can be coupled to or integrated in the user interface 124 or in the conduit 126 to monitor the humidity of the pressurized air from the respiratory therapy device 122. In other implementations, the moisture sensor 176 is placed near any area where moisture levels need to be monitored. The moisture sensor 176 can also be used to monitor the humidity of the ambient environment surrounding the user 210, for example, the air inside the bedroom.

The Light Detection and Ranging (LiDAR) sensor 178 can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 178 can measure and map an area extending 5 meters or more away from the sensor. The LiDAR data can be fused with point cloud data estimated by an electromagnetic RADAR sensor, for example. The LiDAR sensor(s) 178 can also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

In some implementations, the one or more sensors 130 also include a galvanic skin response (GSR) sensor, a blood flow sensor, a respiration sensor, a pulse sensor, a sphygmomanometer sensor, an oximetry sensor, a sonar sensor, a RADAR sensor, a blood glucose sensor, a color sensor, a pH sensor, an air quality sensor, a tilt sensor, a rain sensor, a soil moisture sensor, a water flow sensor, an alcohol sensor, or any combination thereof.

While shown separately in FIG. 1, any combination of the one or more sensors 130 can be integrated in and/or coupled to any one or more of the components of the system 100, including the respiratory therapy device 122, the user interface 124, the conduit 126, the humidification tank 129, the control system 110, the user device 170, the activity tracker 180, or any combination thereof. For example, microphone 140 and the speaker 142 can be integrated in and/or coupled to the user device 170; and the pressure sensor 132 and/or flow rate sensor 134 are integrated in and/or coupled to the respiratory therapy device 122. In some implementations, at least one of the one or more sensors 130 is not coupled to the respiratory therapy device 122, the control system 110, or the user device 170, and is positioned generally adjacent to the user 210 during the sleep session (e.g., positioned on or in contact with a portion of the user 210, worn by the user 210, coupled to or positioned on the nightstand, coupled to the mattress, coupled to the ceiling, etc.).

The data from the one or more sensors 130 can be analyzed to determine one or more sleep-related parameters, which can include a respiration signal, a respiration rate, a respiration pattern, an inspiration amplitude, an expiration amplitude, an inspiration-expiration ratio, an occurrence of one or more events, a number of events per hour, a pattern of events, a sleep state, an apnea-hypopnea index (AHI), or any combination thereof. The one or more events can include snoring, apneas, central apneas, obstructive apneas, mixed apneas, hypopneas, a mask leak, a cough, a restless leg, a sleeping disorder, choking, an increased heart rate, labored breathing, an asthma attack, an epileptic episode, a seizure, increased blood pressure, or any combination thereof. Many of these sleep-related parameters are physiological parameters, although some of the sleep-related parameters can be considered to be non-physiological parameters. Other types of physiological and non-physiological parameters can also be determined, either from the data from the one or more sensors 130, or from other types of data.

The user device 170 (FIG. 1) includes a display device 172. The user device 170 can be, for example, a mobile device such as a smart phone, a tablet, a gaming console, a smart watch, a laptop, or the like. Alternatively, the user device 170 can be an external sensing system, a television (e.g., a smart television) or another smart home device (e.g., a smart speaker(s) such as Google Home, Amazon Echo, Alexa etc.). In some implementations, the user device is a wearable device (e.g., a smart watch). The display device 172 is generally used to display image(s) including still images, video images, or both. In some implementations, the display device 172 acts as a human-machine interface (HMI) that includes a graphic user interface (GUI) configured to display the image(s) and an input interface. The display device 172 can be an LED display, an OLED display, an LCD display, or the like. The input interface can be, for example, a touchscreen or touch-sensitive substrate, a mouse, a keyboard, or any sensor system configured to sense inputs made by a human user interacting with the user device 170. In some implementations, one or more user devices can be used by and/or included in the system 100.

In some implementations, the system 100 also includes an activity tracker 180. The activity tracker 180 is generally used to aid in generating physiological data associated with the user. The activity tracker 180 can include one or more of the sensors 130 described herein, such as, for example, the motion sensor 138 (e.g., one or more accelerometers and/or gyroscopes), the PPG sensor 154, and/or the ECG sensor 156. The physiological data from the activity tracker 180 can be used to determine, for example, a number of steps, a distance traveled, a number of steps climbed, a duration of physical activity, a type of physical activity, an intensity of physical activity, time spent standing, a respiration rate, an average respiration rate, a resting respiration rate, a maximum he respiration art rate, a respiration rate variability, a heart rate, an average heart rate, a resting heart rate, a maximum heart rate, a heart rate variability, a number of calories burned, blood oxygen saturation, electrodermal activity (also known as skin conductance or galvanic skin response), or any combination thereof. In some implementations, the activity tracker 180 is coupled (e.g., electronically or physically) to the user device 170.

In some implementations, the activity tracker 180 is a wearable device that can be worn by the user, such as a smartwatch, a wristband, a ring, or a patch. For example, referring to FIG. 2, the activity tracker 180 is worn on a wrist of the user 210. The activity tracker 180 can also be coupled to or integrated a garment or clothing that is worn by the user. Alternatively still, the activity tracker 180 can also be coupled to or integrated in (e.g., within the same housing) the user device 170. More generally, the activity tracker 180 can be communicatively coupled with, or physically integrated in (e.g., within a housing), the control system 110, the memory device 114, the respiratory therapy system 120, and/or the user device 170.

While the control system 110 and the memory device 114 are described and shown in FIG. 1 as being a separate and distinct component of the system 100, in some implementations, the control system 110 and/or the memory device 114 are integrated in the user device 170 and/or the respiratory therapy device 122. Alternatively, in some implementations, the control system 110 or a portion thereof (e.g., the processor 112) can be located in a cloud (e.g., integrated in a server, integrated in an Internet of Things (IoT) device, connected to the cloud, be subject to edge cloud processing, etc.), located in one or more servers (e.g., remote servers, local servers, etc., or any combination thereof.

While system 100 is shown as including all of the components described above, more or fewer components can be included in a system according to implementations of the present disclosure. For example, a first alternative system includes the control system 110, the memory device 114, and at least one of the one or more sensors 130 and does not include the respiratory therapy system 120. As another example, a second alternative system includes the control system 110, the memory device 114, at least one of the one or more sensors 130, and the user device 170. As yet another example, a third alternative system includes the control system 110, the memory device 114, the respiratory therapy system 120, at least one of the one or more sensors 130, and the user device 170. Thus, various systems can be formed using any portion or portions of the components shown and described herein and/or in combination with one or more other components.

Figure 3A:
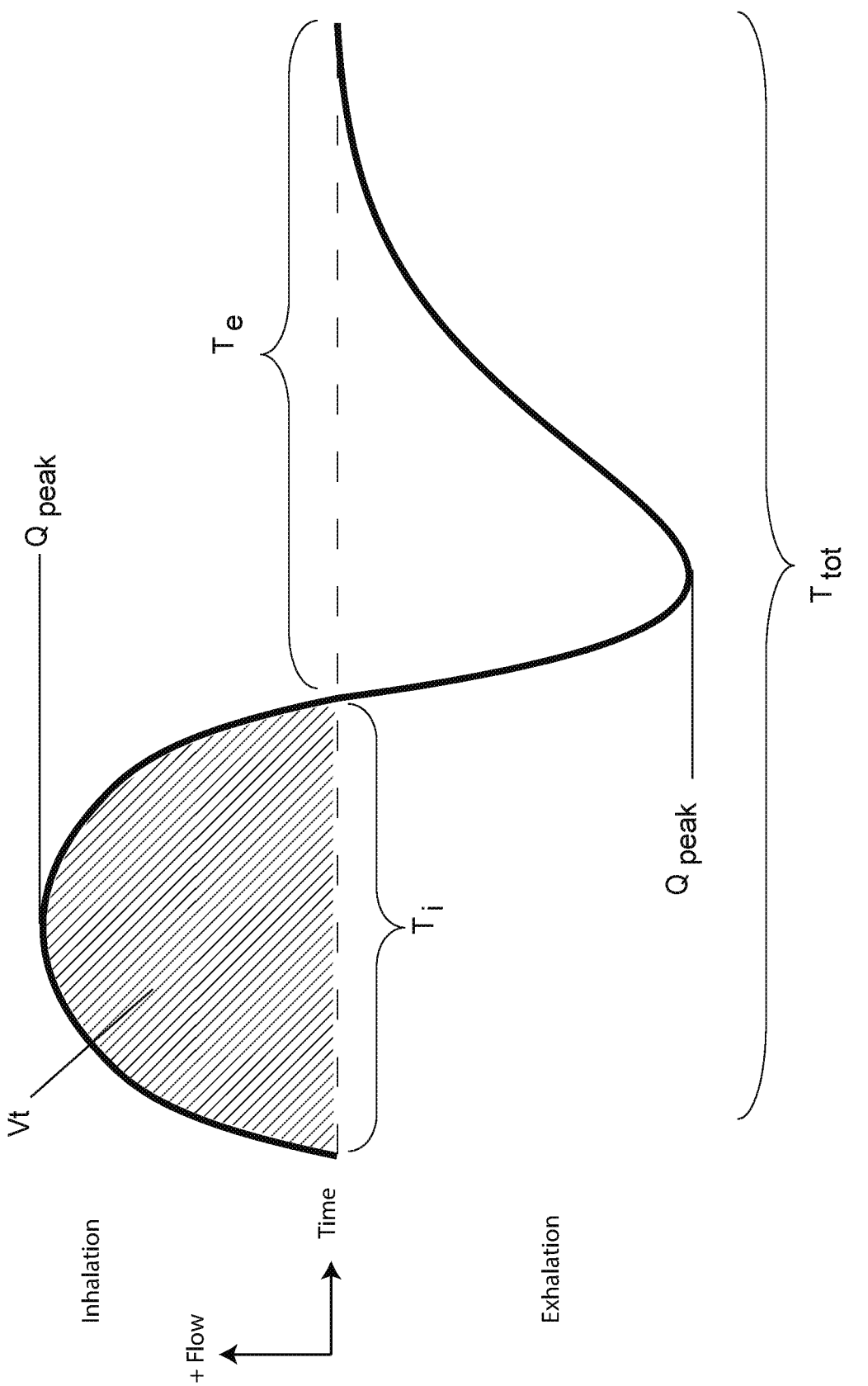
FIG. 3A illustrates a breath waveform of an individual while sleeping, according to some implementations of the present disclosure.

FIG. 3A illustrates a breath waveform of a person while sleeping, according to some implementations of the present disclosure. The horizontal axis is time, and the vertical axis is respiratory flow rate. While the parameter values may vary, an example breathing cycle may have the following approximate values: tidal volume $V_t$ 0.5 L, inhalation time $T_i$ 1.6 s, peak inhalation flow rate $Q_{peak}$ 0.4 L/s, exhalation time $T_e$ 2.4 s, peak exhalation flow rate $Q_{peak}$ –0.5 L/s. The total duration of the breathing cycle, $T_{tot}$, is about four (4) seconds. An individual typically breathes at a rate of about 15 breaths per minute (BPM), with Minute Ventilation about 7.5 L/min. For an example breathing cycle, the ratio of $T_i$ to $T_{tot}$, is about 40%.

Figure 3B:
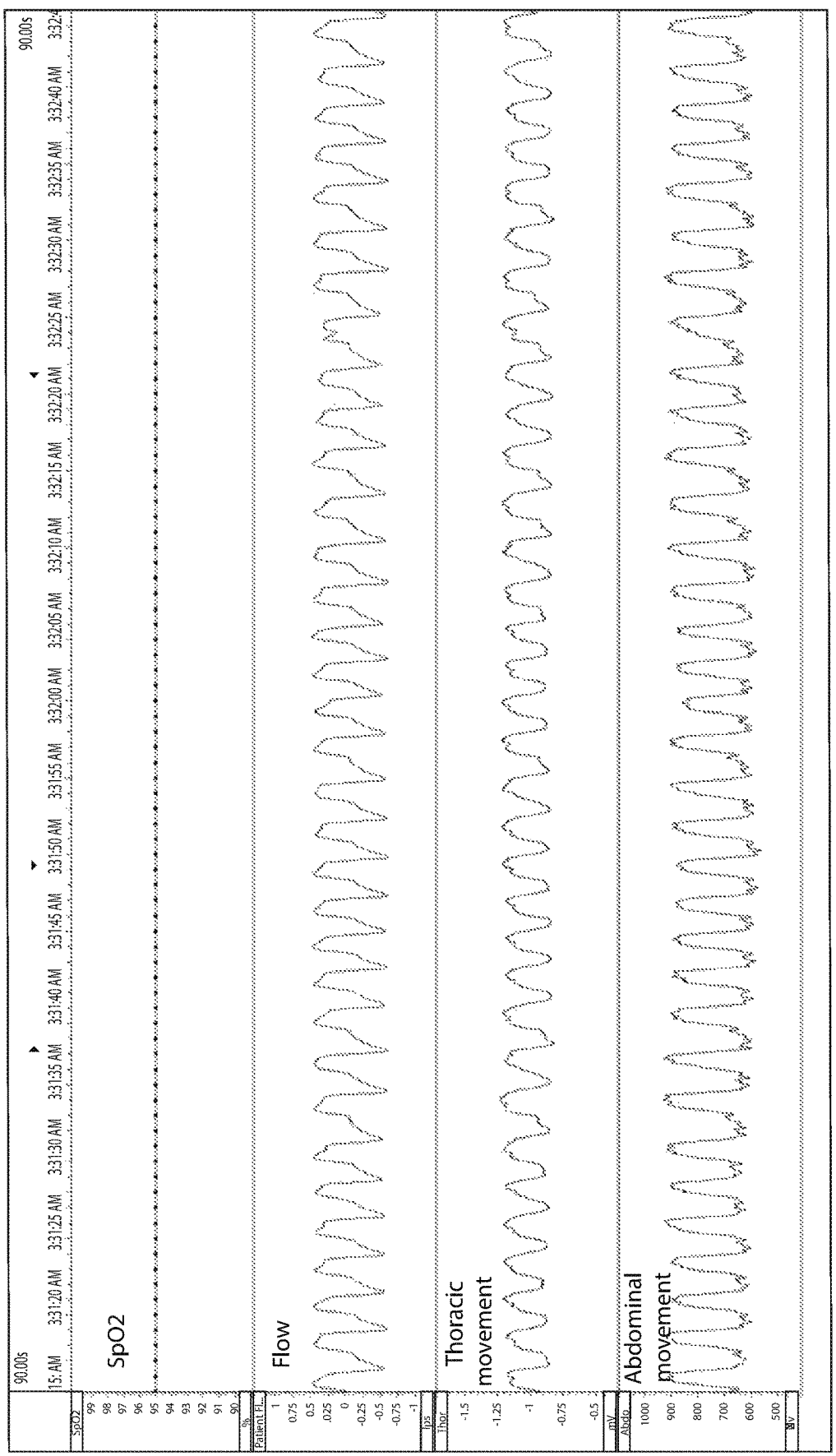
FIG. 3B illustrates selected polysomnography channels (pulse oximetry, flow rate, thoracic movement, and abdominal movement) of an individual during non-REM sleep breathing normally over a period of about ninety seconds, according to some implementations of the present disclosure.

FIG. 3B illustrates selected polysomnography channels (pulse oximetry, flow rate, thoracic movement, and abdominal movement) of an individual during non-REM sleep breathing normally over a period of about ninety seconds, with about 34 breaths, being treated with automatic PAP therapy, and the interface pressure being about 11 cmH$_2$O. The top channel shows pulse oximetry (oxygen saturation or SpO$_2$), and the scale having a range of saturation from 90 to 99% in the vertical direction. The individual maintained a saturation of about 95% throughout the period shown. The second channel shows quantitative respiratory airflow, and the scale ranges from –1 to +1 LPS in a vertical direction, and with inspiration positive. Thoracic and abdominal movement are shown in the third and fourth channels.

Figure 3C:
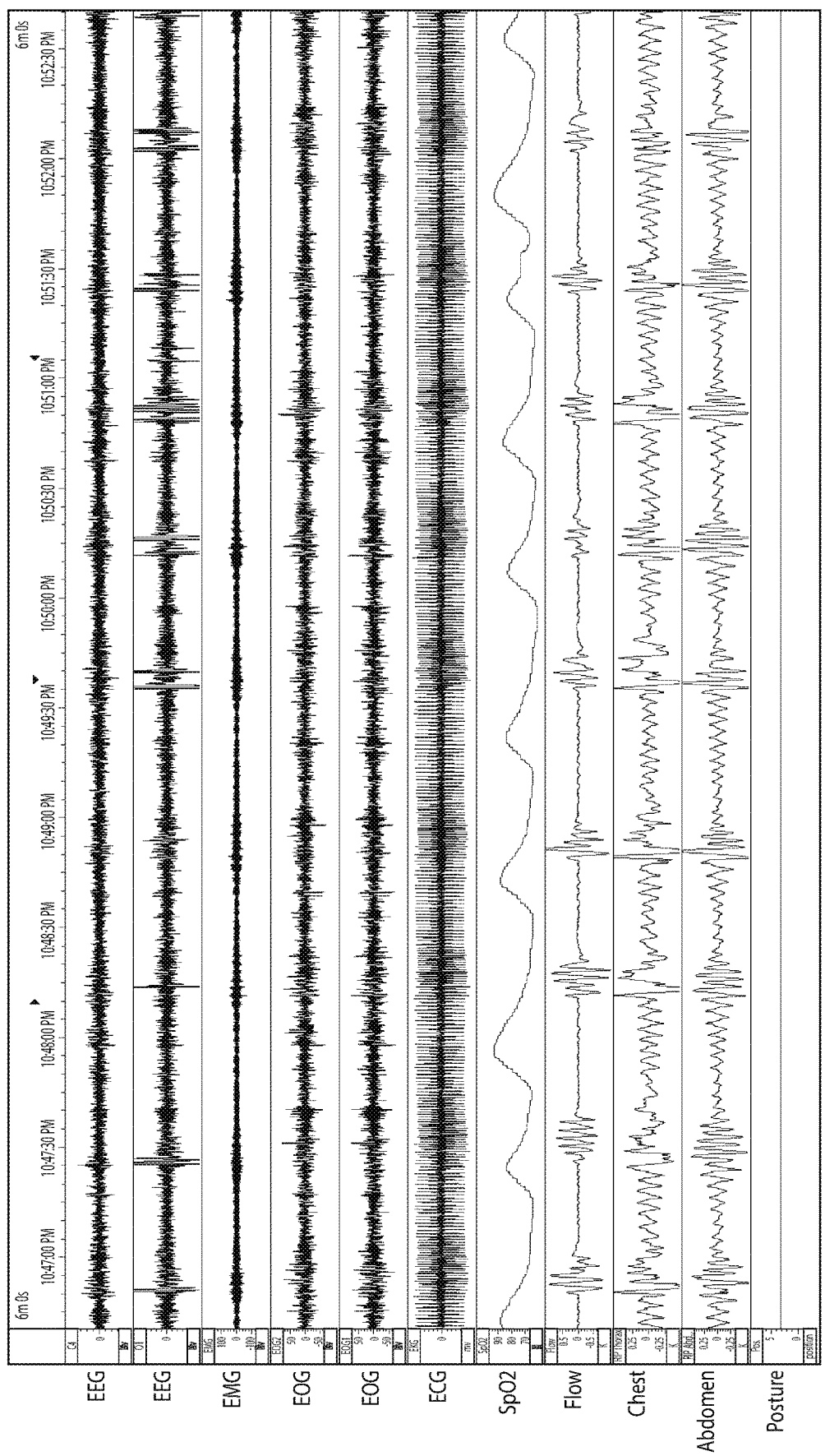
FIG. 3C illustrates polysomnography of an individual before respiratory treatment, according to some implementations of the present disclosure.

FIG. 3C illustrates polysomnography of an individual before treatment, according to some implementations of the present disclosure. There are eleven signal channels from top to bottom with a six-minute horizontal span in time. The top two channels are electroencephalogram (EEG) from different scalp locations. Periodic spikes in the second EEG represent cortical arousal and related activity. The third channel down is submental electromyogram (EMG).

Increasing activity around the time of arousals represents genioglossus recruitment. The fourth and fifth channels are electro-oculogram (EOG). The sixth channel is an electro-cardiogram (ECG). The seventh channel shows pulse oximetry (SpO$_2$) with repetitive desaturations to below 70% from about 90%. The eighth channel is respiratory airflow using a nasal cannula connected to a differential pressure transducer. Repetitive apneas of 25 to 35 seconds alternate with 10 to 15 second bursts of recovery breathing coinciding with EEG arousal and increased EMG activity. The ninth channel shows movement of chest and the tenth shows movement of abdomen. The abdomen shows a crescendo of movement over the length of the apnea leading to the arousal. Both become untidy during the arousal due to gross body movement during recovery hyperpnea. The apneas are therefore obstructive, and the condition is severe. The lowest channel is posture, and in this example, it does not show change.

Figure 3D:
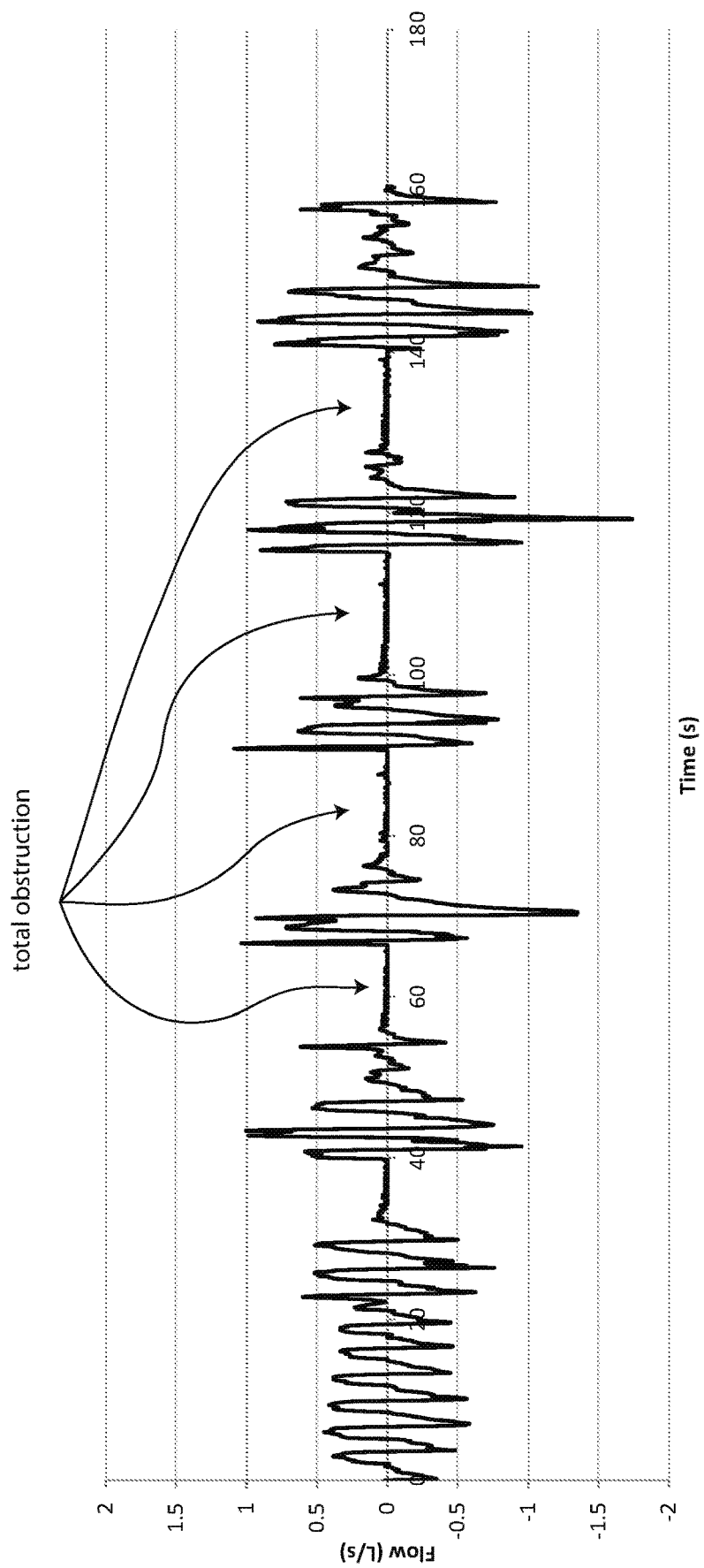
FIG. 3D illustrates flow rate data where an individual is experiencing a series of total obstructive apneas, according to some implementations of the present disclosure.

FIG. 3D illustrates flow rate data where an individual is experiencing a series of total obstructive apneas, according to some implementations of the present disclosure. The duration of the recording is approximately 160 seconds. Flow rates range from about +1 L/s to about –1.5 L/s. Each apnea lasts approximately 10-15 s.

Figure 4A:
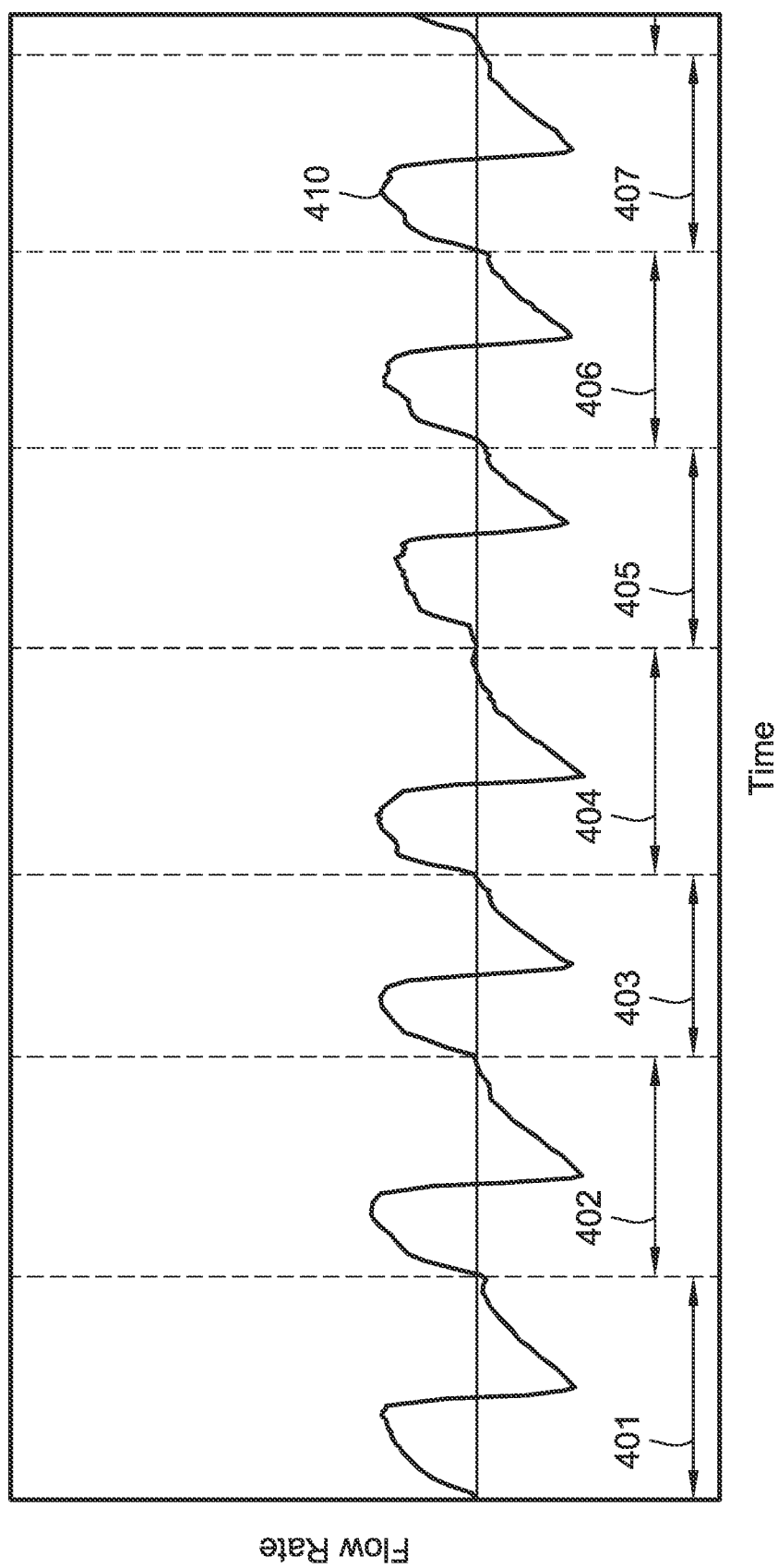
FIG. 4A illustrates flow rate data associated with a user of a respiratory therapy system, according to some implementations of the present disclosure.

In some implementations, the system of the present disclosure includes a flow rate sensor (e.g., the flow rate sensor 134 of FIG. 1) and a pressure sensor (e.g., the pressure sensor 132 of FIG. 1). The flow rate sensor is configured to generate flow rate data over a period of therapy time. For example, FIG. 4A illustrates a portion of such flow rate data associated with a user (e.g., the user 210 of FIG. 2) of a respiratory therapy system (e.g., the respiratory therapy system 120 of FIG. 1), according to some implementations of the present disclosure. As shown in FIG. 4A, a plurality of flow rate values measured over about seven full breathing cycles (401-407) is plotted as a continuous curve 410.

Figure 4B:
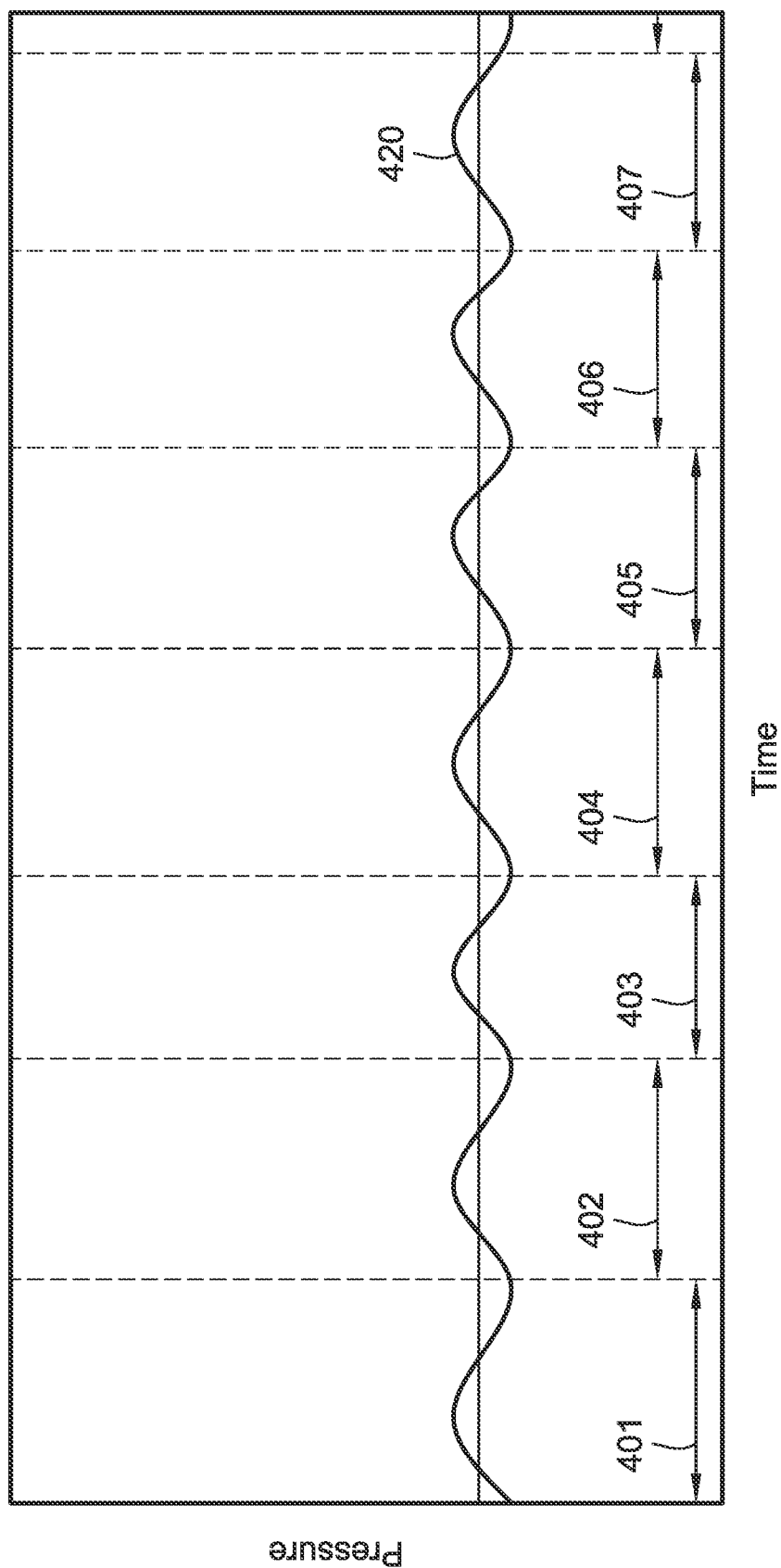
FIG. 4B illustrates pressure data associated with a user of a respiratory therapy system, according to some implementations of the present disclosure.

In some implementations, the pressure sensor is configured to generate pressure data over a period of therapy time. For example, FIG. 4B illustrates pressure data associated with a user of a CPAP system, according to some implementations of the present disclosure. The pressure data shown in FIG. 4B was generated over the same period of therapy time as that of FIG. 4A. As shown in FIG. 4B, a plurality of pressure values measured over about seven full breathing cycles (401-407) is plotted as a continuous curve 420. Because a CPAP system is used, the continuous pressure curve of FIG. 4B exhibits a generally sinusoidal pattern with a relatively small amplitude, because the CPAP system attempts to maintain the constant predetermined air pressure for the system during the seven full breathing cycles.

Figure 4C:
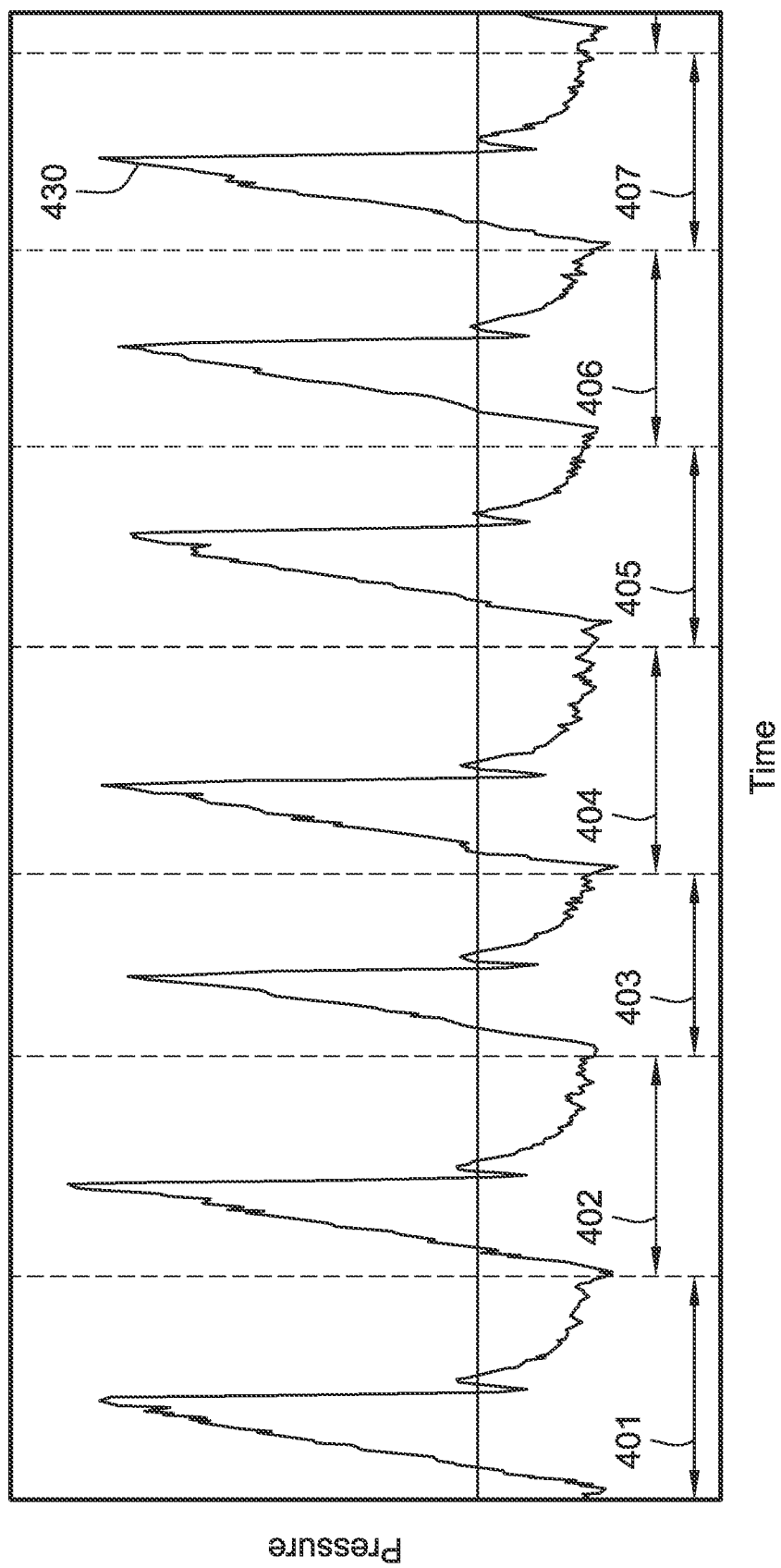
FIG. 4C illustrates pressure data associated with a user of a respiratory therapy system with an expiratory pressure relief module, according to some implementations of the present disclosure.

Referring to FIG. 4C, pressure data associated with a user of a respiratory therapy system with an expiratory pressure relief (EPR) module is illustrated, according to some implementations of the present disclosure. The pressure data shown in FIG. 4C was generated over the same period of therapy time as that of FIG. 4A. As shown in FIG. 4C, a plurality of pressure values measured over about seven full breathing cycles (401-407) is plotted as a continuous curve 430. The continuous curve of FIG. 4C is different from that of FIG. 4B, because the EPR module (used for the pressure data in FIG. 4C) can have different settings for an EPR level, which is associated with the difference between a pressure level during inspiration and a reduced pressure level during expiration.

Figure 12:
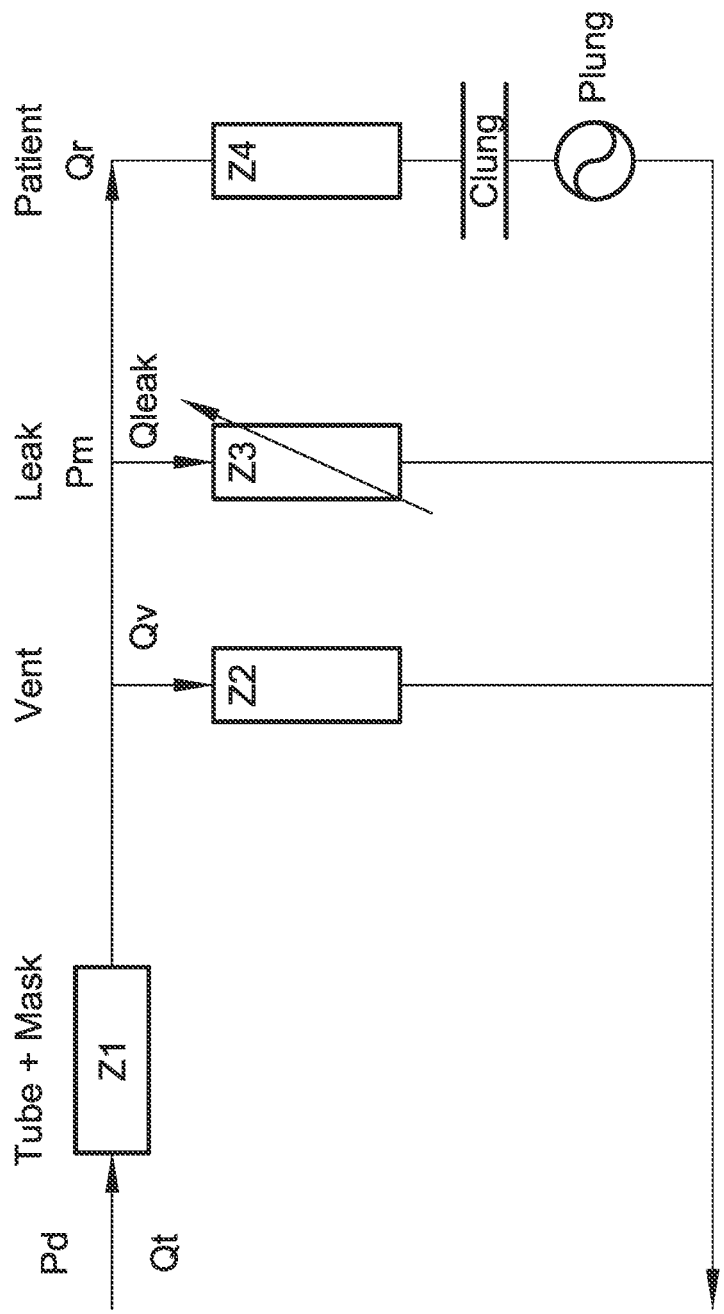
FIG. 12 illustrates four types of impedances (Z1, Z2, Z3, and Z4) affecting the intentional leak characteristic algorithm, according to some implementations of the present disclosure.

Receiving as inputs the plurality of flow rate values (e.g., FIG. 4A) over a time period and the corresponding plurality of pressure values (e.g., FIG. 4B or FIG. 4C) over the time period, an intentional leak characteristic algorithm of the present disclosure can output an intentional leak characteristic curve for the respiratory therapy system associated with the user. As discussed herein, in some implementations, a pathway is formed by a respiratory therapy device (e.g., the respiratory therapy device 122), a mask (e.g., the user interface 124), and a conduit (e.g., the conduit 126). The conduit creates a first impedance Z1 (humidifier tub, tube, and mask impedance, as depicted in FIG. 12), which in turn causes a pressure drop ΔP that is a function of the total flow rate Qt. The user interface (e.g., mask) pressure Pm is the device pressure Pd less the pressure drop ΔP through the conduit.

$$Pm = Pd - \Delta P \quad (1)$$

where ΔP is the pressure drop, characteristic of the conduit. The pressure drop ΔP is a function of the total flow rate Qt:

$$\Delta P = Z1 \cdot Qt \quad (2)$$

In some implementations, the vent of the mask creates a second impedance Z2 (vent impedance, as depicted in FIG. 12). The mask interface pressure Pm is directly related to the vent flow rate Qv via the vent impedance characteristic Z2:

$$Pm = Z2 \cdot Qv \quad (3)$$

Similarly, the vent flow rate Qv is directly related to the mask interface pressure Pm via the vent admittance characteristic Y2:

$$Qv = Y2 \cdot Pm \quad (5)$$

Combining equation (1) with equation (5), the vent flow rate Qv may be determined as:

$$Qv = Y2 \cdot (Pd - \Delta P) \quad (6)$$

The unintentional leak, which is unknown and unpredictably variable, creates a third impedance Z3 (leak impedance, as depicted in FIG. 12). Additionally, in some implementations, the fourth impedance (airway resistance and lung compliance, as depicted in FIG. 12) includes (i) the patient airway resistance Z4, (ii) the patient lung compliance Clung, and/or (iii) the variable pressure source Plung, each of which represents characteristics of the user's respiratory circuit. Thus, the total flow rate Qt is equal to the sum of the vent flow rate Qv, the leak flow rate Qleak, and the respiratory flow rate Qr:

$$Qt = Qv + Qleak + Qr \quad (7)$$

In some implementations, the respiratory flow rate Qr averages to zero over a plurality of respiratory cycles (e.g., breathing cycles), because the average respiratory flow rate into or out of the lungs must be zero. Taking tilde (~) to indicate the average value over the plurality of respiratory cycles:

$$\tilde{Q}r = 0 \quad (8)$$

As such, taking an average of each flow rate over the plurality of respiratory cycles (e.g., breaths), the average leak flow rate may be approximated as:

$$\tilde{Q}leak = \tilde{Q}t - \tilde{Q}v \quad (9)$$

The process of averaging may be implemented by low-pass filtering with a time constant long enough to contain the plurality of respiratory cycles. The time constant can be of any suitable duration, such as five seconds, ten seconds, thirty seconds, one minute, etc. However, other time intervals are also contemplated.

Combining equations (1), (2), and (3), the average device pressure $\tilde{P}d$ may be written as:

$$\tilde{P}d = Z1 \cdot \tilde{Q}t + Z2 \cdot \tilde{Q}v \quad (10)$$

In the absence of any leak flow (e.g., $\tilde{Q}leak=0$), the average total flow rate $\tilde{Q}t$ is equal to the average vent flow rate $\tilde{Q}v$. Equation (10) can then be written to reflect the relationship between the average total flow rate $\tilde{Q}t$ and the average device pressure $\tilde{P}d$ that characterizes the respiratory therapy air circuit:

$$\tilde{P}d = Z1 \cdot \tilde{Q}t + Z2 \cdot \tilde{Q}t \quad (11)$$

$$\tilde{P}d = (Z1 + Z2) \cdot \tilde{Q}t \quad (12)$$

$$\tilde{P}d = (Z1 + Z2) \cdot \tilde{Q}v \quad (13)$$

The relationship, which defines the intentional leak characteristic curve for the system, is determined by the vent impedance characteristic Z2 and the conduit pressure drop impedance characteristic Z1. In the presence of leak, $\tilde{Q}t > \tilde{Q}v$. In the absence of leak, $\tilde{Q}t = \tilde{Q}v$.

Referring now to FIG. 5A, a scatter plot 500a of average total flow rate $\tilde{Q}t$ (in liters per minute) versus average device pressure $\tilde{P}d$ (in cmH$_2$O) is depicted. FIG. 5A illustrates plotted Cartesian coordinates representing average device pressure and average total flow rate, expressed as liters per minute ("LPM," which is equivalent to 60 times L/s). Each Cartesian coordinate includes an X value and a Y value. As shown, five Cartesian coordinates 510, 512, 514, 516, and 518 are plotted in the scatter plot 500a over a period of therapy. Each Cartesian coordinate may also be expressed as ($\tilde{Q}t$, $\tilde{P}d$).

For example, a first Cartesian coordinate 512 has a first X value that is about 20 liters per minute, and a first Y value that is about 6 cmH$_2$O. As such, the first Cartesian coordinate 512 can be expressed as (20, 6). The first X value can be estimated and/or calculated based at least on a first plurality of flow rate values generated over a first time period. In some implementations, the first X value is an average flow rate value of the first plurality of flow rate values generated over the first time period.

In some implementations, the first time period is a predetermined time interval, such as five seconds, ten seconds, 30 seconds, one minute, two minutes etc. In some implementations, the first time period includes one or more full breathing cycles, such as one breathing cycle, two breathing cycles, five breathing cycles, ten breathing cycles, etc. Therefore, in some implementations, the first X value is the average flow rate value of the first plurality of flow rate values generated over one or more breathing cycles, such as seven breathing cycles (FIG. 4A).

Similarly, the first Y value can be estimated and/or calculated based at least on a first plurality of pressure values generated over the first time period. Each of the first plurality of pressure values corresponds with a respective one of the first plurality of flow rate values. For example, in some implementations, each of the first plurality of flow rate values has a corresponding time stamp (e.g., FIG. 4A). Using the corresponding time stamp, the respective one of the first plurality of pressure values can be identified (e.g., FIG. 4B or FIG. 4C). Therefore, in some implementations, the first Y value is the average pressure value of the first plurality of pressure values generated over one or more breathing cycles, such as seven breathing cycles (e.g., FIG. 4B or FIG. 4C).

A second Cartesian coordinate 516 has a second X value that is about 28 liters per minute, and a second Y value that is about 10 cmH$_2$O. As such, the second Cartesian coordinate 516 can be expressed as (28, 10). The second X value and the second Y value of the second Cartesian coordinate 516 can be estimated and/or calculated the same way as, or similar to, the first X value and the first Y value of first Cartesian coordinate 512.

Referring to FIG. 5B, based at least in part on the first Cartesian coordinate 512 and the second Cartesian coordinate 516, an intentional leak characteristic curve 550 can be fitted in the plot 500b. For example, in some implementations, the intentional leak characteristic curve 550 may be approximated using a polynomial equation, such as a quadratic equation:

$$\tilde{P}_d = k_1 \cdot \tilde{Q}_v^2 + k_2 \cdot \tilde{Q}_v \quad (14)$$

The parameters of the intentional leak characteristic curve, in this quadratic equation, two non-zero constants (or coefficients), $k_1$ and $k_2$, characterize the series concatenation of the vent impedance characteristic Z1 and the air circuit pressure drop impedance characteristic Z2. In some implementations, the polynomial equation defines an intentional leak of the system (e.g., vent flow of the system) by providing a corresponding flow rate of intentional leak for a given pressure.

If at least two Cartesian coordinates are known, the non-zero constants $k_1$ and $k_2$ can be solved. For example, using the first Cartesian coordinate 512 (20, 6) and the second Cartesian coordinate 516 (28, 10), equation (8) can be solved and re-written as approximately:

$$\tilde{P}_d = \frac{1}{140} \tilde{Q}_v^2 + \frac{11}{70} \tilde{Q}_v \quad (15)$$

In other words, the non-zero constant $k_1$ is $$\frac{1}{140}$$

(about 0.00714), and the constant $k_2$ is $$\frac{11}{70}$$

(about 0.157) for the quadratic curve going through the first Cartesian coordinate 512 and the second Cartesian coordinate 516. Therefore, in some implementations, the intentional leak characteristic curve 550 can be estimated and/or defined as equation (15).

In some implementations, the non-zero constants depend on (i) the unit for the pressure values, (ii) the unit for the flow rate values, (iii) the vent for the respiratory therapy system, (iv) the mask for the respiratory therapy system, (v) the humidifier tub for the respiratory therapy system, (vi) the conduit for the respiratory therapy system, (vii) computation scaling factors, or (viii) any combination thereof. The non-zero constants can also vary with different types of masks, different manufacturers of masks, and/or different batches of masks. For example, with the pressure values measured in cmH$_2$O and the flow rate values measured in L/min, the non-zero constants $k_1$ and $k_2$ can be about $$\frac{1}{154}$$

and about $$\frac{1}{7}$$

respectively, for a particular vent of a respiratory therapy system.

In some implementations, the polynomial equation may have more than two non-zero constants, such as three non-zero constants, four non-zero constants, five non-zero constants, etc. For example, the polynomial equation may be expressed as:

$$\tilde{P}_d = k_1 \cdot \tilde{Q}_v^2 + k_2 \cdot \tilde{Q}_v + k_3 \quad (16)$$

In some implementations, the polynomial equation may involve a power of three, four, five, etc. For example, the polynomial equation may be expressed as:

$$\tilde{P}_d = k_1 \cdot \tilde{Q}_v^3 + k_2 \cdot \tilde{Q}_v^2 + k_3 \cdot \tilde{Q}_v + k_4 \quad (17)$$

In some implementations, unintentional leak is more likely to occur in a system where the pressure values are high. To get a better fitted intentional leak characteristic curve, only Cartesian coordinates with lower values are used to solve the polynomic equation. For example, in some implementations, the Cartesian coordinates where the Y values do not exceed a predetermined pressure threshold are used. The predetermined pressure threshold may be associated with a low likelihood of unintentional leak, such as less than about 10 cmH$_2$O, less than about 9 cmH$_2$O, less than about 8 cmH$_2$O, less than about 7 cmH$_2$O, less than about 6 cmH$_2$O, less than about 5 cmH$_2$O, less than about 4 cmH$_2$O, less than about 3 cmH$_2$O, or less than about 2 cmH$_2$O.

Figure 7:
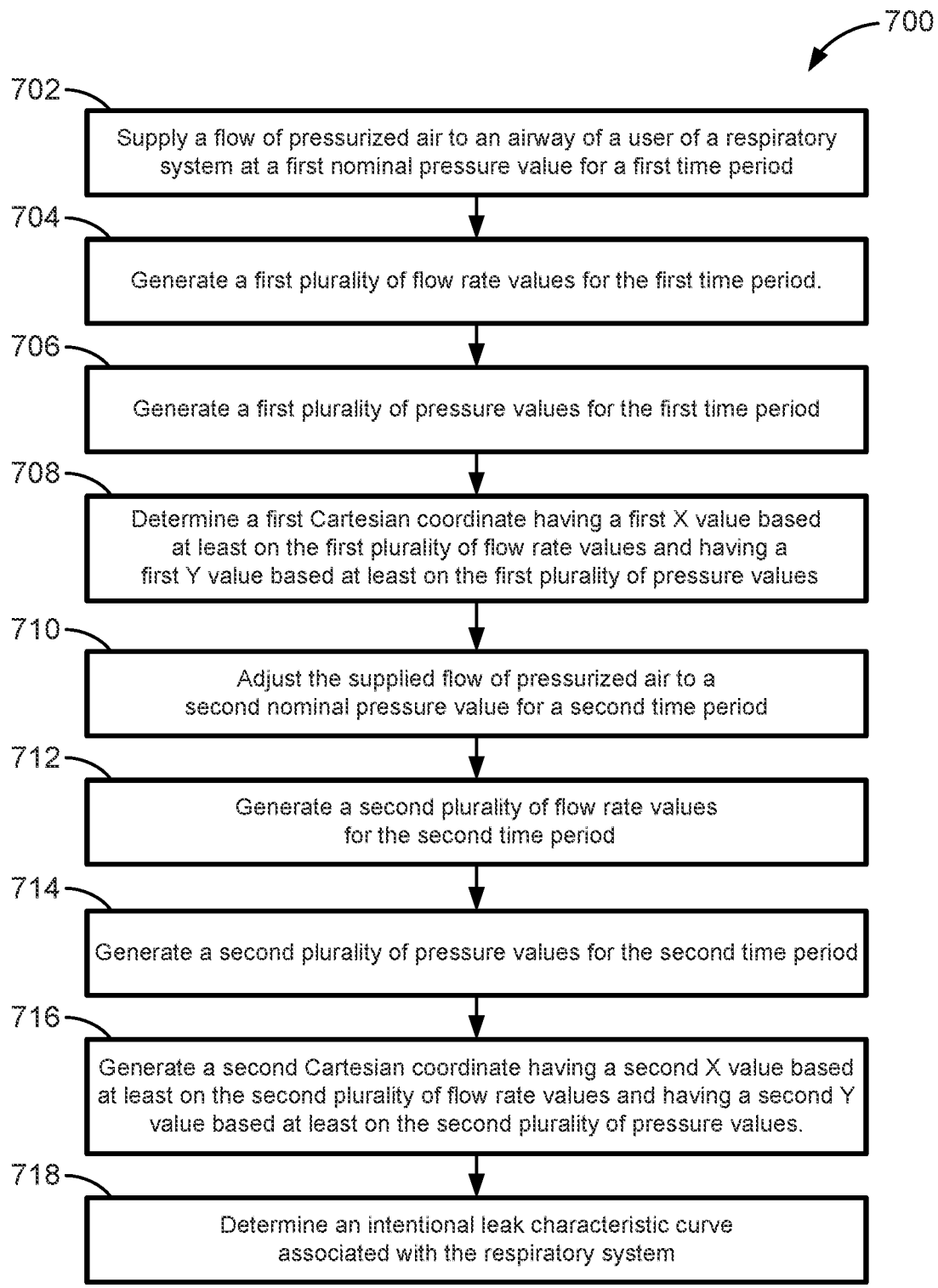
FIG. 7 illustrates a flow diagram for a method of detecting an intentional leak characteristic curve for a respiratory therapy system, according to some implementations of the present disclosure.

As an example, according to some implementations of the present disclosure, a flow diagram for a method (700) of detecting an intentional leak characteristic curve for a respiratory therapy system is illustrated in FIG. 7. The method 700 can be implemented using any of the systems disclosed herein. At step 702 of the method 700, a pressure generator of a respiratory therapy device generates a flow of pressurized air, which is then supplied to an airway of a user for a first time period (e.g., a first one or more sleeping cycles). The flow of pressurized air has a first nominal pressure value. In some implementations, the first nominal pressure value is a pressure that the pressure generator attempts to maintain during operation of the pressure generator, by modifying one or more operating parameters to at least account for breathing of the user. In some such implementations, the one or more operating parameters include a rotation per minute of a motor of the pressure generator, a power supplied to the motor, or a combination thereof.

As described herein, to get a better fitted intentional leak characteristic curve, the first nominal pressure value can be a value not exceeding the predetermined pressure threshold. For example, the first nominal pressure value can be between about 1 cmH$_2$O to about 8 cmH$_2$O, such as 1.5 cmH$_2$O, 2 cmH$_2$O, 2.5 cmH$_2$O, 3 cmH$_2$O, 3.5 cmH$_2$O, 4 cmH$_2$O, 4.5 cmH$_2$O, 5 cmH$_2$O, 5.5 cmH$_2$O, 6 cmH$_2$O, 6.5 cmH$_2$O, 7 cmH$_2$O, 7.5 cmH$_2$O.

While the pressure generator attempts to maintain the first nominal pressure value, at step 704 of the method 700, a first plurality of flow rate values for the first time period is generated using, for example, the flow rate sensor 134. In addition, at step 706 of the method 700, a first plurality of pressure values for the first time period is generated using, for example, the pressure sensor 132. At step 708 of the method 700, a first Cartesian coordinate is determined based on at least one of the first plurality of flow rate values and at least one of the first plurality of pressure values, as describe herein. For example, in some implementations, the first Cartesian coordinate is determined based at least in part on a first flow rate value and a first pressure value. In some implementations, the first Cartesian coordinate is determined based at least in part on an average of the first plurality of flow rate values and an average of the first plurality of pressure values. Alternatively, in some implementations, instead of estimating and/or calculating the first Y value using the first plurality of pressure values, the first nominal pressure value is used as the first Y value.

Once the first Cartesian coordinate is determined, at step 710 of the method 700, the pressure generator adjusts the flow of pressurized air to a second nominal pressure value for a second time period (e.g., a second one or more breathing cycles). In some implementations, the supplied flow of pressurized air is increased to the second nominal pressure value that is greater than the first nominal pressure value. For example, the second nominal pressure value can be between about 0.1 $cmH_2O$ to about 1 $cmH_2O$ greater than the first nominal pressure value, such as 0.1 $cmH_2O$, 0.2 $cmH_2O$, 0.25 $cmH_2O$, 0.5 $cmH_2O$, 0.75 $cmH_2O$, or 1 $cmH_2O$ greater than the first nominal pressure value. Additionally, or alternatively, the second nominal pressure value is between about 0.1% to about 5% greater than the first nominal pressure value, such as 0.1%, 0.15%, 0.2%, 0.25%, 0.3%, 0.35%, 0.4%, 0.45% or 0.5% greater than the first nominal pressure value.

In some implementations, the change between the first nominal pressure value and the second nominal pressure value can be of any suitable value, so long as both the first nominal pressure value and the second nominal pressure value are low enough to cause little unintentional leak of the user. In some implementations, the change between the first nominal pressure value and the second nominal pressure value is small (e.g., between about 0.05 $cmH_2O$ to about 0.1 $cmH_2O$). However, in some such implementations, a change too small (e.g. <0.05 $cmH_2O$) may lead to inaccuracy in the resulting parameter computation (e.g., the estimation of the non-zero constants for the intentional leak characteristic curve).

While the pressure generator attempts to maintain the second nominal pressure value, at step 712 of the method 700, a second plurality of flow rate values for the second time period is generated. In addition, at step 714 of the method 700, a second plurality of pressure values for the second time period is generated. At step 716 of the method 700, a second Cartesian coordinate is determined based on at least one of the second plurality of flow rate values and at least one of the second plurality of pressure values, as describe herein. Alternatively, in some implementations, instead of estimating and/or calculating the second Y value using the second plurality of pressure values, the second nominal pressure value is used as the second Y value.

Similarly, in some implementations, a third, fourth, fifth, or more Cartesian coordinates can be determined while the pressure generator adjusts the flow of pressurized air. Knowing the two or more Cartesian coordinates, at step 718 of the method 700, an intentional leak characteristic curve associated with the respiratory therapy system can be determined using the methods disclosed herein.

Figure 6:
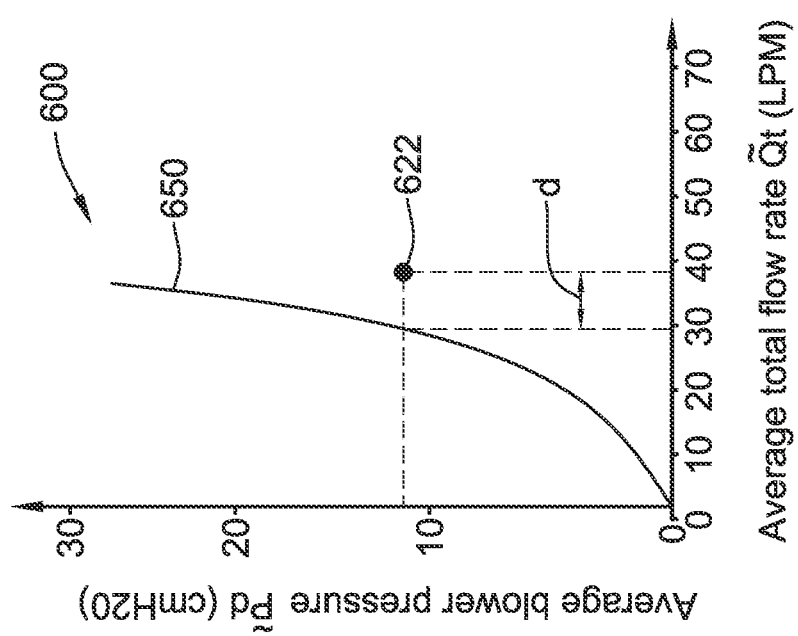
FIG. 6 illustrates an intentional leak characteristic curve of a respiratory therapy system associated with a user, according to some implementations of the present disclosure.

Referring now to FIG. 6, an intentional leak characteristic curve 650 of a respiratory therapy system associated with a user is shown on a plot 600. The intentional leak characteristic curve 650 relates each value of average device pressure $\tilde{P}d$ to the average total flow rate $\tilde{Q}v$ at that value of device pressure. The excursions, e.g. Cartesian coordinate 622, to the right of the intentional leak characteristic curve 650 is indicative of an unintentional leak, which exhibits as an increased flow rate for a given device pressure.

Over a period of respiratory therapy, where the average device pressure $\tilde{P}d$ varies, and absent any unintentional leak, the point ($\tilde{Q}t$, $\tilde{P}d$) moves up and down, following the intentional leak characteristic curve 650. However, having an unintentional leak can cause the point ($\tilde{Q}t$, $\tilde{P}d$) to move to the right of the intentional leak characteristic curve 650 for a period. If the unintentional leak resolves, the point ($\tilde{Q}t$, $\tilde{P}d$) returns to the intentional leak characteristic curve 650. Therefore, the unintentional leak may show up on the plot 600 as excursions to the right of the intentional leak characteristic curve 650.

For example, at a point (shown as Cartesian coordinate 622) where the user experiences an unintentional leak, $\tilde{Q}t$ is greater than the average vent flow $\tilde{Q}v$ at that value of average device pressure $\tilde{P}d$. The difference between the actual $\tilde{Q}t$ and the average vent flow $\tilde{Q}v$ at the given average device pressure $\tilde{P}d$ is the flow offset d, which is about 9 liters per minute, as shown in FIG. 6. On the other hand, excursions to the left of the intentional leak characteristic curve 650, such as the points ($\tilde{Q}t$, $\tilde{P}d$) where $\tilde{Q}t$ is less than the average vent flow $\tilde{Q}v$, may indicate vent blockages (e.g. as a result of head movement relative to the pillow on which the user is sleeping and which causes blockage of vent(s) by the pillow).

As discussed herein, a respiratory therapy system typically includes components such as a respiratory therapy device, a conduit, and a user interface. A variety of different forms of user interface may be used with a given respiratory therapy device, such as nasal pillows, nasal prongs, a nasal mask, a nose and mouth (orinasal) mask, or a full face mask. Furthermore, different lengths and diameters of conduits may be used. In order to provide improved control of therapy delivered to the user interface, it may be advantageous to estimate treatment parameters such as the pressure in the user interface, the vent flow rate, and the unintentional flow rate. In systems using estimation of treatment parameters, knowledge of the type of component being used by a user can enhance the accuracy of treatment parameter estimation, and therefore the efficacy of therapy.

To obtain knowledge of component type, some respiratory therapy devices include a menu system that allows the user to enter and/or select the type of system components, including the user interface being used (e.g., brand, manufacturer, form, model, serial number, mask family, size etc.). Once the types of the components are entered and/or selected by the user, the respiratory therapy device can select appropriate operating parameters of the flow generator that best coordinate with the selected components, and can more accurately monitor treatment parameters during therapy. However, in some instances, the user may not select the type of component correctly, or at all, leaving the respiratory therapy device in error or ignorant about the type of component in use.

As such, in some implementations, the intentional leak characteristic algorithm described herein can be used to identify the user interface. For example, if the conduit pressure drop characteristic ΔP is known, (e.g., because the type of conduit making up the conduit is known, or through a prior calibration operation), then the parameters of the intentional leak characteristic curve effectively characterize the vent, which in turn is indicative of the type of user interface.

In some implementations, the identification of user interface may be done by comparing the computed parameters $k_1$ and $k_2$ to a data structure such as an array or database having pairs ($k_1$, $k_2$) associated with known user interface types, when used with the known conduit. The type of user interface associated with the stored pair ($k_1$, $k_2$) that most closely matches the computed parameters $k_1$ and $k_2$ may be taken as the type of the user interface.

Alternatively, the pressure drop $\Delta P = Z1 \cdot \tilde{Q}t$ may be subtracted from each value of the average device pressure $\tilde{P}d$ before fitting the quadratic equation to the resulting mask intentional leak characteristic curve. The resulting parameters $k_1$ and $k_2$ may then be compared to a data structure of pairs ($k_1$, $k_2$) associated with known user interface types to identify the user interface or access data for operations of the respiratory therapy device that is associated with use of particular user interfaces.

Thus, the detected parameters can be compared to the expected parameters over a period of time, collecting longitudinal data and cross-sectional data. In some implementations, the system may be able to determine production variation by understanding a batch of masks, and use this for production quality improvement.

In some implementations, the system can check for variation over time, and understand if the mask seal itself is degrading over time (as the system can determine how long a specific mask has been in use based on an RFID tag and/or user input), and what are the conditions that are giving rise to unintentional leak (e.g., is it position dependent, has it changed based on recommendation to tighten or loosen headgear, has the seal followed an expected degradation cycle (assuming regular washing), is it showing accelerated wear, etc.).

In some implementations, the user interface being used can be determined by: user input, detecting the user interface optically, detecting the user interface via RFID, detecting the user interface using electronics (e.g., a user interface detection component), detecting the conduit via a connector of a heated tube that has electronics (e.g., electronic connection connecting to a control system of a respiratory therapy device, an electronic chip, etc.), or any combination thereof. Thus an initial curve can be selected that describes a correctly functioning new mask of this type. The initial curve may be specific to the respiratory therapy device, the operating mode, the operating parameters, other settings such as EPR or bi-level, the user interface (e.g., brand, manufacturer, form, model, serial number, mask family, size etc.), or any combination thereof.

In some implementations, over time, the system may also be able to select models of expected behavior of partially worn or fully worn out masks of this type as the initial curve, such as from a look up table, or from a cloud system. These expected models may describe different levels of vent occlusion, conduit occlusion (such as for masks that have airflow through soft tubing around the head) and different levels of seal wear, headgear stretching and so forth. Thus, by selecting an appropriate initial model, the system can detect intentional leak and unintentional leak through a sleep session, and/or across multiple sleep sessions.

In some implementations, the system may be able to detect low intentional leak (e.g., lower than expected intentional leak), early indications of vent blockage (e.g., excess moisture, ageing and so forth), and/or poor sleep position of the user (such as occluding vent). In some such implementations, prompts can be sent to the user (i) to alert the user of these issues, (ii) to recommend replacement of the mask and/or vent, or (iii) both.

In some implementations, the system may be able to detect bed pillows blocking the exhalation ports. In some such implementations, prompts can be sent to the user to suggest a change of bedding, a change in mask configuration, a change in mask type, or any combination thereof.

Further, in some implementations, unintentional leak can also occur around the humidifier tub/seal. This can manifest as a high pitched sound (audible and potentially annoying to some people with higher frequency hearing, such a bed partner of the user), as well as another source of "intentional leak" that is not associated with the vent flow. In order to avoid confusing with seal unintentional leak, the system may also process acoustic sounds to check if the signature of such humidifier tub leak is present. The system may recommend to the user to re-seat the tub. By separating this source of leak, a more accurate separation of leak type (and suggested resolution) can be provided to the user and/or health care professional.

Having a more robust and/or accurate model of the leak reporting will result in more users remaining as users, e.g., these users might otherwise have discontinued use as a result of inconsistent and/or inaccurate leak reporting. In some implementations, the present disclosure may provide systems and methods for determining if a mouth leak is occurring, which allows a recommendation to the user for a full face mask, before the user quits therapy from problems with nasal masks and the resulting mouth leak.

Generally, a user who is prescribed usage of a respiratory system will tend to experience higher quality sleep and less fatigue during the day after using the respiratory therapy system 120 during the sleep compared to not using the respiratory therapy system 120 (especially when the user suffers from sleep apnea or other sleep related disorders). However, many users do not conform to their prescribed usage because the user interface 124 is uncomfortable or cumbersome, or due to other side effects (e.g., dry mouth, dry lips, dry throat, discomfort, etc.). Users are more likely to fail to use the respiratory therapy system 120 as prescribed (or discontinue usage altogether) if they fail to perceive that they are experiencing any benefits (e.g., less fatigue during the day).

However, the side effects and/or the lack of improvement in sleep quality may be due to mouth leak rather than a lack of efficacy to the treatment. Thus, it is advantageous to determine a mouth leak status for the user, and communicate the mouth leak status to the user to aid the user in obtaining higher quality sleep, so that the user does not discontinue or reduce their usage of the respiratory therapy system 120 due to a perceived lack of benefit(s).

In some implementations, selecting the mask type setting on the respiratory therapy device is not necessary. The present disclosure provides an automatic system of detecting the mask type by estimating the intentional leak characteristic curve, and comparing the estimated intentional leak characteristic curve to existing data for the particular mask type (e.g., from a lookup table, from other users of the same mask type, from previous data associated with the same user, or any combination thereof).

According to some implementations of the present disclosure, alternative or additional methods (e.g., method 800 of FIG. 8) can be used to determine an intentional leak characteristic curve for a respiratory therapy system (e.g., the respiratory therapy system 120 of FIG. 1). These methods improve mask (e.g., the user interface 124) impedance determination and/or tube (e.g., the conduit 126) impedance determination, which can in some implementations be characterized by the intentional leak characteristic curve. Benefits of improved impedance determination include: (i) improving leak estimation accuracy, (ii) resolving underreporting of mask leak, (iii) providing impedance feature input to assist the identification of the mask, (iv) providing diffuser loss feature input to assist the estimation and/or determination of mouth leak, (v) exploiting air circuit signals and/or impedance.

In some implementations, the methods disclosed herein utilize a CPAP air flow circuit model. In some implementations, the methods disclosed herein may be based at least in part on breath synchronization, which reduces and/or removes the confounding factor of a user's breathing when determining the intentional leak characteristic curve. In some such implementations, the impedance determination methods disclosed herein remove the confounding breathing signal, which results in more precise and/or accurate impedance determination.

Figure 8:
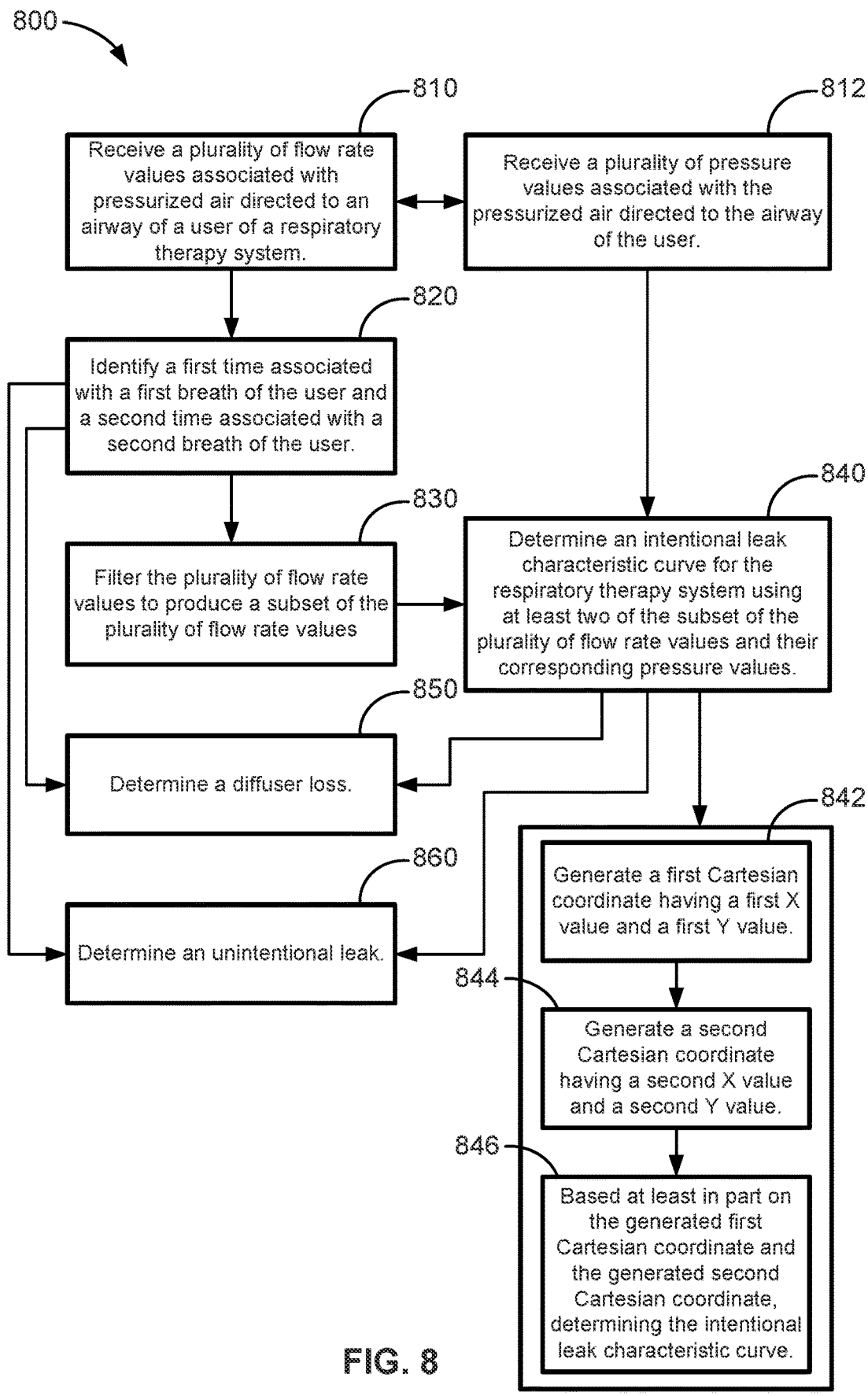
FIG. 8 illustrates a flow diagram for a method of determining an intentional leak characteristic curve for a respiratory therapy system, according to some implementations of the present disclosure.

Referring to FIG. 8, method 800 for determining an intentional leak characteristic curve for a respiratory therapy system is disclosed, according to some implementations of the present disclosure. In some implementations, one or more steps of the method 800 may be similar to, a part of, or an alternative of one or more steps the method 700. In some other implementations, one or more steps of the method 800 may include one or more steps of the method 700.

As disclosed herein, in some implementations, the continuous time filter (or sampling) is replaced by a "start of inhale and/or exhale" breath-by-breath sampling. Some advantages of this approach to impedance determination and/or measurement include: (i) the breathing signal, independent of its frequency content, is accurately removed by default, (ii) the intentional leak component is accurately retained, (iii) the impedance flow and pressure signals are down-sampled, reducing computational complexity, (iv) the breathing signal signature can be used to: (a) support the leak threshold, breath by breath, computation, (b) address confounding leak issues (e.g., any unintentional leak such as mouth leak); (v) existing respiratory (e.g. CPAP) system parameters can be utilized, (vi) the breath-by-breath method is additionally advantageous for bi-level flow filtering.

At step 810, a plurality of flow rate values associated with pressurized air directed to an airway of a user (e.g., the user 210 of FIG. 2) of the respiratory therapy system (e.g., the respiratory therapy system 120) is received. At step 812, a plurality of pressure values associated with the pressurized air directed to the airway of the user is received. In some implementations, each of the plurality of pressure values corresponds to a respective one of the plurality of flow rate values.

Figure 9:
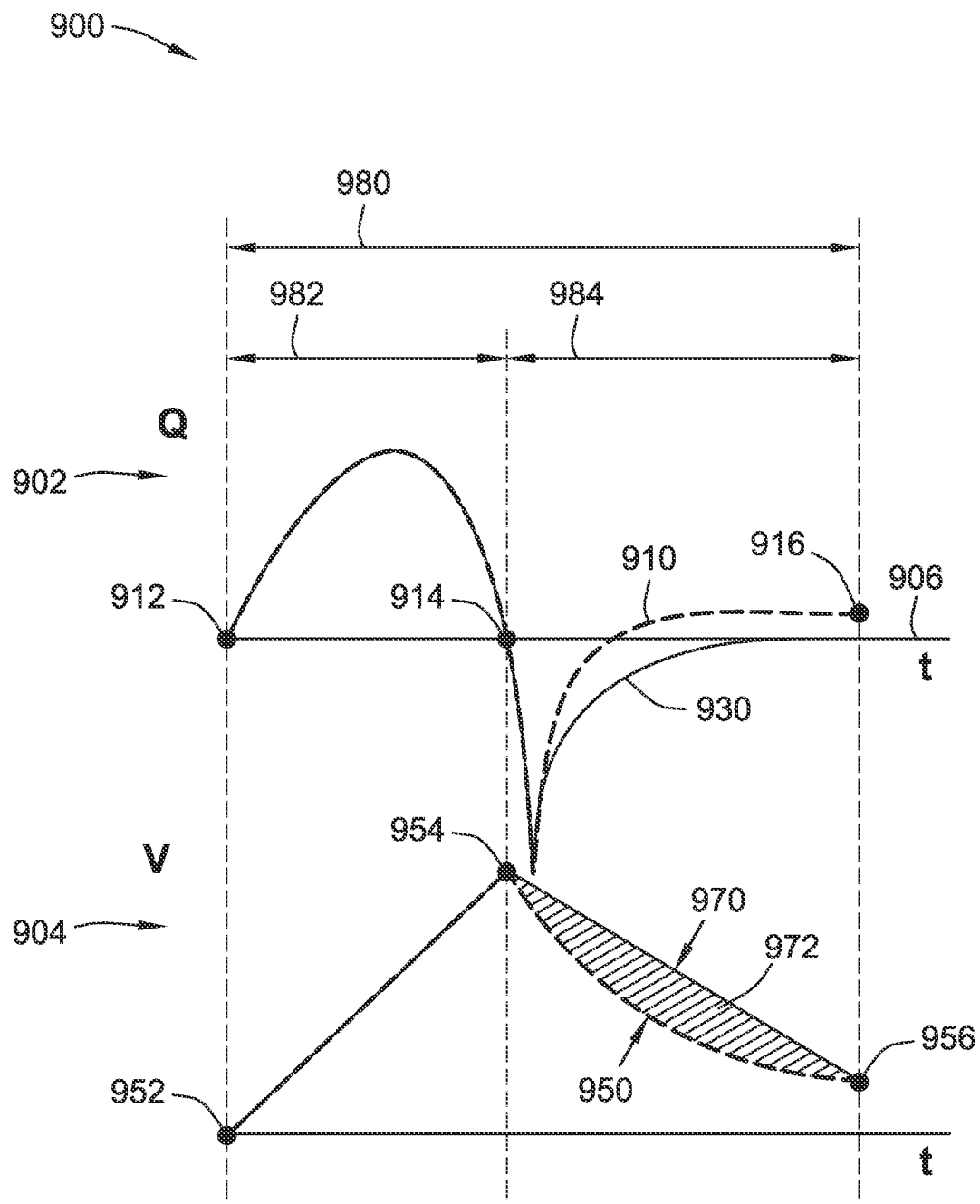
FIG. 9 illustrates flow rate ("Q") data and flow volume ("V") data during a breath under respiratory therapy, according to some implementations of the present disclosure.

At step 820, a first time associated with a first breath of the user and a second time associated with a second breath of the user are identified. In some implementations, the first time and the second time can be identified by analyzing a plurality of corresponding flow volume values of at least a portion of the plurality of flow rate values. In some implementations, the plurality of corresponding flow volume values is determined by taking a time integral of the at least the portion of the plurality of flow rate values. An example method of identifying the first time associated with the first breath of the user is illustrated in FIG. 9. The second time can be identified in the same, or similar manner.

At step 830, the plurality of flow rate values is filtered based at least in part on the identified first time and the identified second time. The filtering then produces a subset of the plurality of flow rate values. In some implementations, the subset of the plurality of flow rate values may include 1% or less of the received plurality of flow rate values. Additionally, or alternatively, in some implementations, the subset of the plurality of flow rate values includes (i) one, two, three, four, or five flow rate values for the first breath and (ii) one, two, three, four, or five flow rate values for the second breath. For example, the subset of the plurality of flow rate values may include (i) one, two, three, four, or five flow rate values at about the beginning of inhalation of the first breath and (ii) one, two, three, four, or five flow rate values at about the beginning of inhalation of the second breath.

In some implementations, the plurality of flow rate values is filtered with a low pass filter, to produce the subset of the plurality of flow rate values that is purely DC (e.g., not including and/or affected by the breathing of the user). The DC value may be an average value—A low pass filter removes the higher frequencies and leaves the low frequency, and hence, an average value. For example, in some implementations, the low pass filter includes first analyzing the flow volume values to identify the first time associated with the first breath of the user and the second time associated with the second breath of the user (step 820). However, any suitable filtering to identify the first time associated with the first breath of the user and the second time associated with the second breath of the user may be employed in the disclosed method.

In some implementations, the filtering the plurality of flow rate values (step 830) includes, or additionally or alternatively includes, filtering out (i) flow rate values affected by a breathing of the user, (ii) flow rate values indicative of a mouth leak of the user, (iii) flow rate values associated with irregular breaths (e.g., the length of time is too long or too short for inhalation, exhalation, or entire breath), or (iv) any combination thereof.

At step 840, the intentional leak characteristic curve for the respiratory therapy system is determined using at least two of the subset of the plurality of flow rate values and their corresponding pressure values. In some implementations, step 840 includes one or more steps of 842, 844, and 846. At step 842, a first Cartesian coordinate having a first X value and a first Y value is generated. The first X value is a first flow rate value corresponding to the first time (identified at step 820). The first Y value is a first pressure value corresponding to the first time. At step 844, a second Cartesian coordinate having a second X value and a second Y value is generated. The second X value is a second flow rate value corresponding to the second time (identified at step 820). The second Y value is a second pressure value corresponding to the second time. At step 846, the intentional leak characteristic curve is determined based at least in part on the generated first Cartesian coordinate and the generated second Cartesian coordinate. For example, in some implementations, systems and methods shown and described with reference to FIGS. 5A-5B and/or FIG. 6 can be utilized at step 840.

In some implementations, the intentional leak characteristic curve is calculated using the equation:

$$Z = \frac{P}{Q} = k_1 Q + k_2 \quad (12)$$

where Z is the intentional leak characteristic curve (e.g., indicative of the impedance), P is a pressure value of the plurality of pressure values, Q is a flow rate value of the plurality of flow rate values, $k_1$ is a first constant, and $k_2$ is a second constant. In some such implementations, the first constant $k_1$ may be associated with the turbulent flow; the second constant $k_2$ may be associated with the laminar flow. The formula (12) is advantageous because the impedance can be calculated using a linear equation.

In some implementations, the method 800 further includes outputs of diffuser loss (step 850) and unintentional leak (step 860). The diffuser loss output (step 850) may include features such as mask identification (e.g., identifying a user interface associated with the respiratory therapy system), mask auto setting (e.g., adjusting one or more settings associated with the user interface), and/or mouth leak detection (e.g., determining a mouth leak associated with the user of the respiratory therapy system). The unintentional leak output (step 860) may include features such as mouth leak detection and/or user leak correction.

Referring to FIG. 9, flow rate data ("Q") and flow volume data ("V") during a first breath under respiratory therapy are illustrated, according to some implementations of the present disclosure. The plot 900 illustrates the first breath 980 of a user of a respiratory therapy system. In some implementations, each breath of the user includes an inhalation portion and an exhalation portion. As shown, the first breath 980 includes the inhalation portion 982 and the exhalation portion 984. The upper section 902 of the plot 900 shows the flow rate data 910 (dashed line) associated with the user over the first breath 980. The lower section 904 of the plot 900 shows the corresponding flow volume data 950 (dashed line). In some implementations, the corresponding flow volume data 950 can be determined by taking a time integral of the flow rate data 910.

The flow volume data can be used to identify the first time associated with the first breath of the user and the second time associated with the second breath of the user (e.g., step 820 of the method 800), which can then be used to determine the intentional leak characteristic curve (e.g., step 840 of the method 800). In some implementations, the first time is within the inhalation portion of the first breath and the second time is within the inhalation portion of the second breath.

In some implementations, the first time is when the first breath of the user began and the second time is when the second breath of the user began. Additionally or alternatively, in some implementations, the first time is about a beginning and/or commencement of the inhalation portion of the first breath and the second time is about a beginning of the inhalation portion of the second breath. In this example shown in FIG. 9, the first time may correspond to flow rate 912 of the flow rate data 910 and flow volume 952 of the flow volume data 950. The flow volume 952 is the minimum flow volume value during the first breath 980.

In some such implementations, the minimum flow volume value (e.g., flow volume 952) for the first breath 980 corresponds to the beginning of the first breath 980 and/or the beginning of the inhalation portion 982 of the first breath 980. Thus, the first time may be identified by analyzing the flow volume data 950 to find the minimum flow volume value. The minimum flow volume value (e.g., flow volume 952) for the first breath 980 also corresponds to the flow rate 912, which is the flow rate at the beginning of inspiration (Q="zero" flow rate is shown in FIG. 9 as the horizontal line 906).

In some implementations, the first time is within the exhalation portion of the first breath and the second time is within the exhalation portion of the second breath. Additionally or alternatively, in some implementations, the first time is about a beginning of the exhalation portion of the first breath and the second time is about a beginning of the exhalation portion of the second breath. In this example shown in FIG. 9, the first time may correspond to flow rate 914 of the flow rate data 910 and flow volume 954 of the flow volume data 950. The flow volume 954 is the maximum flow volume value during the first breath 980.

In some such implementations, the maximum flow volume value (e.g., flow volume 954) for the first breath 980 corresponds to the beginning of the exhalation portion 984 of the first breath 980. Thus, the first time may be identified by analyzing the flow volume data 950 to find the maximum flow volume value. The maximum flow volume value (e.g., flow volume 954) for the first breath 980 also corresponds to the flow rate 914, which is the "zero" flow rate (i.e. the flow rate at the point in the user's breathing cycle between inspiration and expiration).

Identifying the times when the flow rate is zero can be advantageous because the confounding breathing signal is excluded (i.e., when the flow rate is not zero). However, in some examples when the user is experiencing unintentional leak (e.g., mouth leak), the flow rate may not return to zero at the end of a breath. In this example of FIG. 9, at the end of the first breath 980, the flow rate 916 has not returned to the "zero" flow rate. In contrast, where the user is experiencing no unintentional leak, the flow rate data 930 shows the end flow volume returns to "zero".

To determine the existence and/or the amount of unintentional leak for the first breath 980, the flow volume data can be analyzed by comparing an end flow volume 956 associated with the end of the first breath 980 to the beginning flow volume 952 associated with the beginning of the first breath 980. Based at least in part on the comparison, whether the user is experiencing unintentional leak (e.g., mouth leak indicative of air leaking from a mouth of the user) during the first breath 980 can be determined. The end flow volume 956 being greater than the beginning flow volume 952 is indicative of the user experiencing the unintentional leak during the first breath 980. In response to the determination that the user is experiencing unintentional leak during the first breath 980, the first breath 980 may be excluded in determining the intentional leak characteristic curve for the respiratory therapy system (step 840 of FIG. 8).

Additionally or alternatively, in some implementations, the amount of unintentional leak during the first breath 980 may be determined by analyzing the flow volume data. In this example of FIG. 9, the area difference 972 between the flow volume data 950 and the reference data 970 is indicative of the amount of unintentional leak during the first breath 980. For the inhalation portion 982, the reference data 970 aligns with the flow volume data 950, thus the user likely experiences no unintentional leak during the inhalation portion 982. For the exhalation portion 984, the reference data 970 plots as a straight line between the maximum flow volume 954 to the end flow volume 956. The area difference 972 can be calculated by subtracting a first time integral of flow volume values in the flow volume data 950 from a second time integral of flow volume values in the reference data 970.

Figure 10:
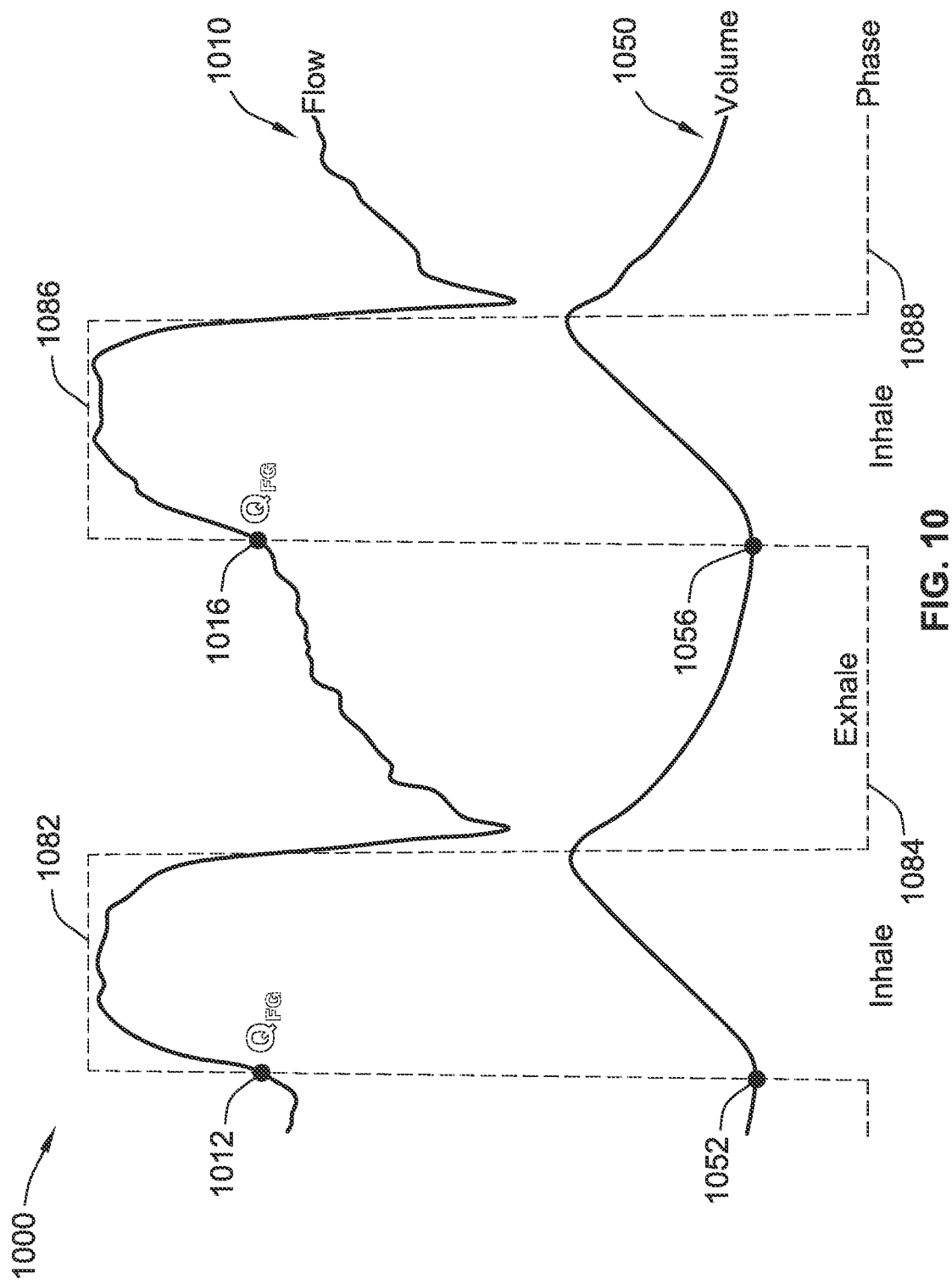
FIG. 10 illustrates flow rate data and flow volume data during two breaths under respiratory therapy, according to some implementations of the present disclosure.

As another example of implementing one or more steps of the method 800 (FIG. 8), FIG. 10 illustrates flow rate data and flow volume data during two breaths under respiratory therapy, according to some implementations of the present disclosure. The upper portion of the plot 1000 shows flow rate versus time. The lower portion of the plot 1000 shows the corresponding flow volume versus time. The flow volume data 1050 can be calculated by taking a time integral of the flow rate data 1010. The flow rate data 1010 and the flow volume data 1050 are plotted over two breaths. The first breath includes the first inhalation portion 1082 and the first exhalation portion 1084. The second breath includes the second inhalation portion 1086 and the second exhalation portion 1088.

In this example of FIG. 10, the flow rate 1012 and the flow volume 1052 correspond to the first time; the flow rate 1016 and the flow volume 1056 correspond to the second time. Thus, the first time is when the first breath of the user began and the second time is when the second breath of the user began. Additionally or alternatively, the first time is about the beginning of the inhalation portion 1082 of the first breath and the second time is about a beginning of the inhalation portion 1086 of the second breath. Further additionally or alternatively, the first time corresponds to the minimum flow volume value of the first breath, and the second time corresponds to a minimum flow volume value of the second breath.

Figure 11:
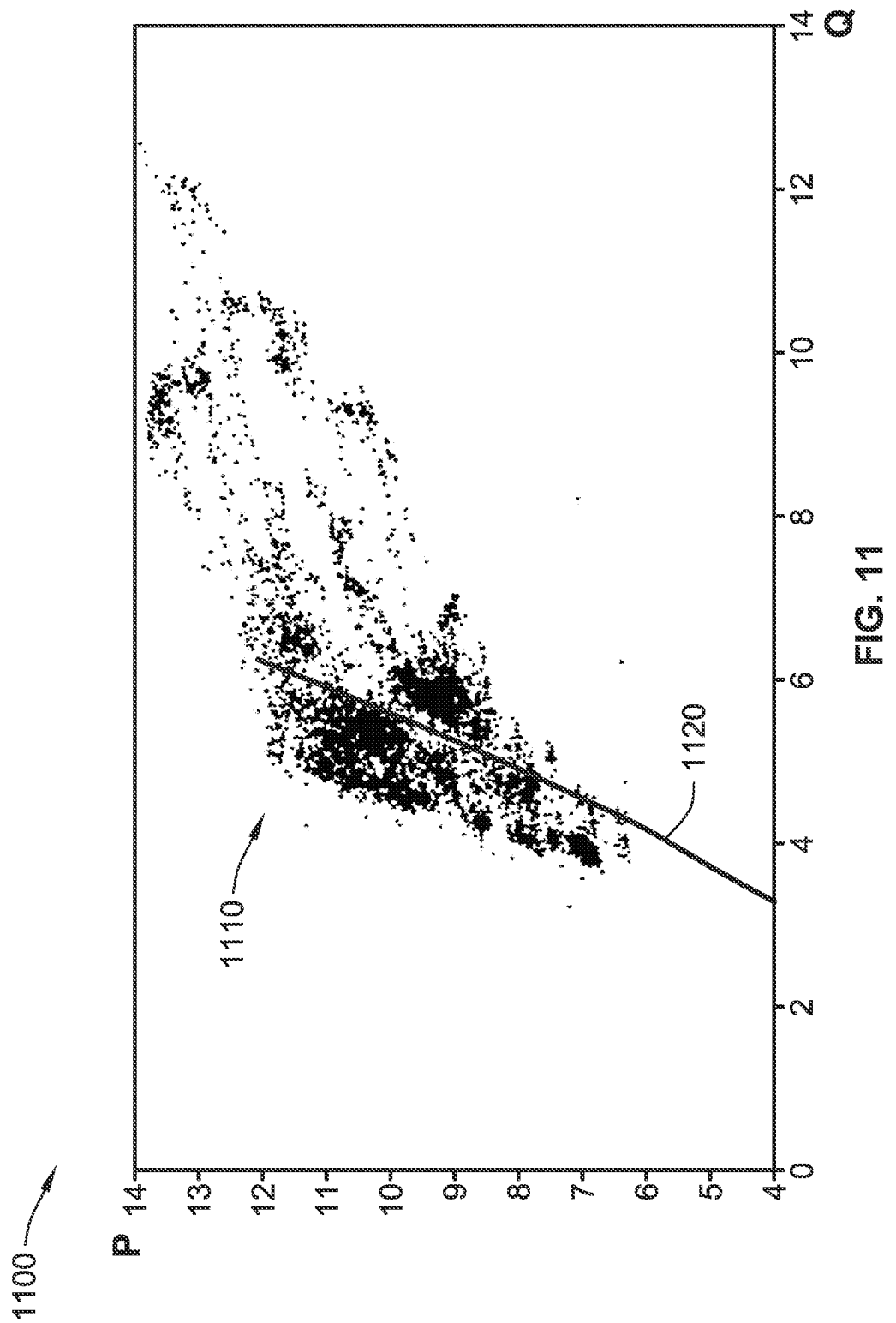
FIG. 11 illustrates an intentional leak characteristic curve fitted for a scatter plot of pressure values ("P"; cmH2O) versus flow rate values ("Q"; liters per 10 s), according to some implementations of the present disclosure.

Referring to FIG. 11, an intentional leak characteristic curve fitted for scatter plot 1100 (pressure versus flow rate) is illustrated, which may implement one or more steps of the methods disclosed herein, such as step 840 of the method 800. The X-axis represents the flow rate values ("Q," liters per 10 seconds), and the Y-axis represents the pressure values ("P," cmH$_2$O). For each breath, a Cartesian coordinate having a first X value and a first Y value is plotted, as a point in the scatter points 1110. The first X value of a first Cartesian coordinate is a first flow rate value corresponding to the first time (identified at step 820 of the method 800). The first Y value of the first Cartesian coordinate is a first pressure value corresponding to the first time (identified at step 820 of the method 800). The subsequent Cartesian coordinates are plotted in the same, or similar manner as the first Cartesian coordinate. Then, the intentional leak characteristic curve 1020 is fitted to the scatter points 1110.

In some implementations, some Cartesian coordinates of the scatter points 1110 are excluded during the fitting of the intentional leak characteristic curve 1020. For example, the Cartesian coordinates corresponding to the breaths during which the user experiences unintentional leak may be excluded, as further disclosed above.

In some implementations, the patient impedance can be determined once the PAP air circuit impedance is known. The circuit modeling suggests the patient impedance determination method can be implemented. In some implementations, the patient impedance determination method can determine if mouth breathing can be differentiated from nasal breathing for full face masks. In some such implementations, additional information associated with leak phases can improve the differentiation between mouth breathing and nasal breathing.

One or more elements or aspects or steps, or any portion(s) thereof, from one or more of any of claims 1-127 below can be combined with one or more elements or aspects or steps, or any portion(s) thereof, from one or more of any of the other claims 1-127 or combinations thereof, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A method for determining an intentional leak characteristic curve for a respiratory therapy system, comprising:
   receiving a plurality of flow rate values associated with pressurized air directed to an airway of a user of the respiratory therapy system;
   receiving a plurality of pressure values associated with the pressurized air directed to the airway of the user, each of the plurality of pressure values corresponding to a respective one of the plurality of flow rate values;
   identifying a first time associated with a first breath of the user and a second time associated with a second breath of the user;
   filtering the plurality of flow rate values based at least in part on the identified first time and the identified second time, the filtering producing a subset of the plurality of flow rate values; and
   determining the intentional leak characteristic curve for the respiratory therapy system using at least two of the subset of the plurality of flow rate values and the corresponding pressure values for said at least two of the subset of the plurality of flow rate values.

2. The method of claim 1, wherein the determining the intentional leak characteristic curve for the respiratory therapy system includes:
   generating a first Cartesian coordinate having a first X value and a first Y value, the first X value being a first flow rate value corresponding to the first time, the first Y value being a first pressure value corresponding to the first time;
   generating a second Cartesian coordinate having a second X value and a second Y value, the second X value being a second flow rate value corresponding to the second time, the second Y value being a second pressure value corresponding to the second time; and
   based at least in part on the generated first Cartesian coordinate and the generated second Cartesian coordinate, determining the intentional leak characteristic curve.

3. The method of claim 1, wherein the intentional leak characteristic curve is calculated using the equation:

$$Z = \frac{P}{Q} = k_1 Q + k_2$$

wherein Z is the intentional leak characteristic curve, P is a pressure value of the plurality of pressure values, Q is a flow rate value of the plurality of flow rate values, $k_1$ is a first constant, and $k_2$ is a second constant.

4. The method of claim 3, wherein the first time corresponds to a minimum flow volume value of the first breath, and the second time corresponds to a minimum flow volume value of the second breath.

5. The method of claim 1, further comprising:
determining, for at least a portion of the plurality of flow rate values, a plurality of corresponding flow volume values.

6. The method of claim 5, wherein the first time associated with the first breath of the user and the second time associated with the second breath of the user are identified based at least in part on analyzing the determined plurality of corresponding flow volume values.

7. The method of claim 5, further comprising:
comparing an end flow volume value associated with an end of the first breath to a beginning flow volume value associated with a beginning of the first breath; and
based at least in part on the comparison, determining that the user is experiencing mouth leak during the first breath, the mouth leak being indicative of air leaking from the user's mouth.

8. The method of claim 7, wherein the beginning flow volume value is a minimum flow volume value of the first breath.

9. The method of claim 7, wherein the end flow volume value being greater than the beginning flow volume value is indicative of the user experiencing the mouth leak during the first breath.

10. The method of claim 7, further comprising:
in response to the determination that the user is experiencing mouth leak during the first breath, excluding the first breath in determining the intentional leak characteristic curve for the respiratory therapy system.

11. The method of claim 1, wherein a first flow rate value corresponding to the first time equals an initial flow rate value at a beginning of the first breath;
and wherein a second flow rate value corresponding to the second time equals an initial flow rate value at a beginning of the second breath.

12. The method of claim 11, wherein the initial flow rate value at the beginning of the first breath and the initial flow rate value at the beginning of the second breath are the same.

13. The method of claim 1, wherein the filtering the plurality of flow rate values includes filtering out (i) flow rate values affected by a breathing of the user, (ii) flow rate values indicative of a mouth leak of the user, (iii) flow rate values associated with irregular breaths, or (iv) any combination thereof.

14. The method of claim 1, further comprising based at least in part on the determined intentional leak characteristic curve, determining a diffuser loss.

15. The method of claim 14, further comprising based at least in part on the determined diffuser loss, (i) identifying a user interface associated with the respiratory therapy system, (ii) adjusting one or more settings associated with the user interface, (iii) determining a mouth leak associated with the user of the respiratory therapy system, or (iv) any combination thereof.

16. The method of claim 1, wherein the subset of the plurality of flow rate values includes 1% or less of the plurality of flow rate values.

17. The method of claim 1, wherein the subset of the plurality of flow rate values includes (i) one, two, three, four, or five flow rate values for the first breath and (ii) one, two, three, four, or five flow rate values for the second breath.

18. A method for determining an intentional leak characteristic curve for a respiratory therapy system, comprising:
receiving a plurality of flow rate values associated with pressurized air directed to an airway of a user of the respiratory therapy system, wherein each of the plurality of flow rate values is associated with a first time in each of a plurality of breaths of the user;
receiving a plurality of pressure values associated with the pressurized air directed to the airway of the user, each of the plurality of pressure values corresponding to a respective one of the plurality of flow rate values;
determining the intentional leak characteristic curve for the respiratory therapy system using at least two of a subset of the plurality of flow rate values and the corresponding pressure values for said at least two of the subset of the plurality of flow rate values.

19. The method of claim 18, wherein the determining the intentional leak characteristic curve for the respiratory therapy system includes:
generating a first Cartesian coordinate having a first X value and a first Y value, the first X value being a first flow rate value corresponding to the first time associated with a first breath, the first Y value being a first pressure value corresponding to the first time associated with the first breath;
generating a second Cartesian coordinate having a second X value and a second Y value, the second X value being a second flow rate value corresponding to the first time associated with a second breath, the second Y value being a second pressure value corresponding to the first time associated with the second breath; and
based at least in part on the generated first Cartesian coordinate and the generated second Cartesian coordinate, determining the intentional leak characteristic curve.

20. The method of claim 18, wherein the intentional leak characteristic curve is calculated using the equation:

$$Z = \frac{P}{Q} = k_1 Q + k_2$$

wherein Z is the intentional leak characteristic curve, P is a pressure value of the plurality of pressure values, Q is a flow rate value of the plurality of flow rate values, $k_1$ is a first constant, and $k_2$ is a second constant.

21. The method of claim 20, wherein the first time corresponds to a minimum flow volume value in each breath.

22. The method of claim 18, further comprising:
determining, for at least a portion of the plurality of flow rate values, a plurality of corresponding flow volume values.

23. The method of claim 22, wherein the first time associated with a first breath of the user and the first time associated with a second breath of the user are identified based at least in part on analyzing the determined plurality of corresponding flow volume values.

24. The method of claim 22, further comprising:
comparing an end flow volume value associated with an end of a first breath to a beginning flow volume value associated with a beginning of the first breath; and
based at least in part on the comparison, determining that the user is experiencing mouth leak during the first breath, the mouth leak being indicative of air leaking from the user's mouth.

25. The method of claim 24, wherein the beginning flow volume value is a minimum flow volume value of the first breath.

26. The method of claim 24, wherein the end flow volume value being greater than the beginning flow volume value is indicative of the user experiencing the mouth leak during the first breath.

27. The method of claim 24, further comprising:
in response to the determination that the user is experiencing mouth leak during the first breath, excluding the first breath in determining the intentional leak characteristic curve for the respiratory therapy system.

28. The method of claim 18, wherein a first flow rate value corresponding to the first time equals an initial flow rate value at a beginning of each breath.

29. The method of claim 28, wherein the initial flow rate value at the beginning of a first breath and the initial flow rate value at the beginning of a second breath are the same.

30. The method of claim 18, wherein the filtering the plurality of flow rate values includes filtering out (i) flow rate values affected by a breathing of the user, (ii) flow rate values indicative of a mouth leak of the user, (iii) flow rate values associated with irregular breaths, or (iv) any combination thereof.

31. The method of claim 18, further comprising based at least in part on the determined intentional leak characteristic curve, determining a diffuser loss.

32. The method of claim 31, further comprising based at least in part on the determined diffuser loss, (i) identifying a user interface associated with the respiratory therapy system, (ii) adjusting one or more settings associated with the user interface, (iii) determining a mouth leak associated with the user of the respiratory therapy system, or (iv) any combination thereof.

33. The method of claim 18, wherein the subset of the plurality of flow rate values includes 1% or less of the plurality of flow rate values.

34. The method of claim 18, wherein the subset of the plurality of flow rate values includes (i) one, two, three, four, or five flow rate values for a first breath and (ii) one, two, three, four, or five flow rate values for a second breath.

* * * * *